(12) United States Patent
Baeza-Ramirez et al.

(10) Patent No.: US 7,867,723 B2
(45) Date of Patent: Jan. 11, 2011

(54) METHOD FOR ANTIPHOSPHOLIPID SYNDROME

(75) Inventors: Maria Isabel Baeza-Ramirez, Mexico (MX); José Leopoldo Aguilr-Faisal, Mexico (MX); Carlos Wong-Ramirez, Mexico (MX); Miguel Angel Ibáñez Hernández, Mexico (MX); Mónica Lara-Uc, Mexico (MX)

(73) Assignee: Escuela Nacional De Ciencias Biologicas, Del Instituto Politecnico Nacional, Colonia Santo Tomas (MX)

( * ) Notice: Subject to any disclaimer, the term of this patent is extended or adjusted under 35 U.S.C. 154(b) by 179 days.

(21) Appl. No.: 10/866,163

(22) Filed: Jun. 14, 2004

(65) Prior Publication Data

US 2004/0224374 A1 Nov. 11, 2004

Related U.S. Application Data

(62) Division of application No. 09/632,735, filed on Aug. 4, 2000, now Pat. No. 6,777,193.

(51) Int. Cl.
*G01N 33/53* (2006.01)
*G01N 21/00* (2006.01)

(52) U.S. Cl. ............... 435/7.21; 435/7.1; 435/7.95; 436/501; 436/518; 422/60

(58) Field of Classification Search .......... 435/7.1, 435/7.2, 7.21, 7.92, 7.94, 174, 176, 177, 435/287.1, 287.2, 287.9, 975, 965, 875; 436/506, 436/507, 513, 518, 519, 524, 528, 533, 534, 436/536, 538, 547, 548, 811, 815, 71, 829; 422/68.1; 424/184.1, 283.1, 810, 812, 155.1, 424/156.1, 277.1, 450; 530/359, 868
See application file for complete search history.

(56) References Cited

U.S. PATENT DOCUMENTS

| | | | |
|---|---|---|---|
| 4,444,879 A * | 4/1984 | Foster et al. | 435/7.95 |
| 4,698,299 A | 10/1987 | Janoff et al. | |
| 5,344,758 A | 9/1994 | Krillis et al. | |
| 5,472,883 A | 12/1995 | Matsuura et al. | |
| 5,506,110 A | 4/1996 | Matsuura et al. | |
| 5,561,070 A | 10/1996 | Stewart et al. | |
| 5,610,024 A | 3/1997 | Muller-Berghaus et al. | |
| 5,776,487 A | 7/1998 | Wilson et al. | |
| 5,780,319 A | 7/1998 | Wilson et al. | |
| 5,840,587 A * | 11/1998 | Stewart et al. | 436/513 |
| 5,998,223 A | 12/1999 | Matsuura et al. | |
| 6,284,475 B1 | 9/2001 | Rand | |
| 6,406,693 B1 * | 6/2002 | Thorpe et al. | 424/130.1 |
| 6,824,988 B2 * | 11/2004 | Roelens et al. | 435/7.1 |
| 6,824,999 B1 * | 11/2004 | Robichaud et al. | 435/7.92 |

OTHER PUBLICATIONS

Wilson, W.A. et al. International consensus statement on preliminary classification criteria for definite antiphospholipid syndrome. Arthritis Rheum. 1999;42:1309-1311.*
Ortiz, A. et al. Membrane fusion and the lamellar-to-inverted-hexagonal phase transition in cardiolipin vesicle systems induced by divalent cations. Biophys. J. 1999;77:2003-2014.*
American College of Rheumatology, History of the ACR, available at <http://www.rheumatology.org> (last update unknown). p. 1 of 1.*
Ramirez et al., Induccibn y Caracterizacibn de Anticuerpos Antifosfolipidos Obtenidos en Ratones BaIB/c Tratados con Cloropromacina, Procainamida y Liposomas, Instituto Politecnico Nacional, Mexico, D.F., 1998.*
Aguilar et al., "Phospholipid Membranes Form Specific Nonbilayer Molecular Arrangements That Are Antigenic," The Journal of Biological Chemistry 274(36):25193-25196, 1999.
Alving, "Immunologic aspects of liposomes: presentation and processing of liposomal protein and phospholipid antigens," Biochim. Biophys. Acta 1113:307-22, 1992.
Arvieux, "Development of an ELISA for Autoantibodies to Prothrombin Showing their Prevalence in Patients with Lupus Anticoagulants," Thromb Haemost 74(4):1120-5, 1995.
Asherson et al., The Antiphospholipid Syndrome: History, Definition, Classification, and Differential Diagnosis, Chapter I, pp. 3-12, CRC Press, Inc., 1996.
Baeza et al., "Transbilayer Diffusion of Divalent Cations into Liposomes Mediated by Lipidic Particles of Phosphatidate," J. Mol. Evol. 39:560-568, 1994.
Baeza et al., "Identification of phosphatidate nonlamellar phases on liposomes by flow cytometry," Biochem. Cell Biol. 73:289-297, 1995.
Berard et al., "Plasma reactivity to hexagonal II phase phosphatidylethanolamine is more frequently associated with lupus anticoagulant than with antiphosphatidylethanolamine antibodies," J. Lab. Clin. Med. 122(5):601-605, 1993.
Bevers et al., "Lupus Anticoagulant IgG's (LA) Are Not Directed to Phospholipids only, but to a Complex of Lipid-Bound Human Prothrombin," Thromb Haemost 66(6):629-32, 1991.
Biasiolo et al., "Antiphospholipid antibodies are not present in the membrane of gel-filtered platelets of patients with IgG anticardiolipin antibodies, lupus anticoagulant and thrombosis," Blood Coagulation Fibrinolysis 4:425-428, 1993.
Cullis et al., "Lipid Polymorphism," Membrane Fusion, pp. 35-64, Marcel Dekker, New York, 1991.
Faisal, "Detección de Anticuerpos Contra Particulas Lipídicas en el Suero de Pacientes con Síndrome de Antifosfolípidos," Instituto Politecnico Nacional, Mexico, D.F., 1999.

(Continued)

*Primary Examiner*—Lisa V Cook
(74) *Attorney, Agent, or Firm*—Rothwell, Figg, Ernst & Manbeck, P.C.

(57) ABSTRACT

Methods for detecting anti-lipidic particle antibodies and lipidic particles in cellular membranes for the diagnosis of diseases associated with antiphospholipid syndrome are disclosed. Kits or sets to put these methods of diagnosis into practice are disclosed. Methods for the therapeutic treatment of diseases associated with antiphospholipid syndrome are disclosed as well. In addition, methods for the detection of the diverse physiologic states of cells and kits useful for this are also disclosed.

14 Claims, 17 Drawing Sheets

OTHER PUBLICATIONS

Gibson et al., "Combined $_D$-Penicillamine and Chloroquine Treatment of Rheumatoid Arthritis—A Comparative Study," Br J Rheumatol 26(4):279-84, 1987.

Guglielmone et al., Distribution of Lupus Anticoagulant and Anticardiolipin Antobidy Isotypes in a Population with Antiphospholipid Syndrome, The Journal of Rheumatology 26(1):86-90, 1999.

Harris et al., "Anti-phospholipid Antibodies," Clinics in Rheumatic Diseases, 11(3):591-609, Dec. 1985.

Köhler et al., "Continuous cultures of fused cells secreting antibody of predefined specificity," Nature 256:495-497, Aug. 7, 1975.

Loizou et al., "Measurement of anti-cardiolipin antibodies by an enzyme-linked immunosorbent assay (ELISA): standardization and quantitation of results," Clin. exp. Immunol. 62:738-745, 1985.

McNeil et al., "Anticardiolipin antibodies and lupus anticoagulants comprise separate antibody subgroups with different phospholipid binding characteristics," British Journal of Haematology 73:506-513, 1989.

McNeil et al., "Anti-phospholipid antibodies are directed against a complex antigen that includes a lipid-binding inhibitor of coagulation: $\beta_2$-Glycoprotein I (apolipoprotein H)," Proc. Natl. Acad. Sci. USA 87:4120-4124, Jun. 1990.

Nakamura et al., "Lupus Anticoagulant Autoantibody Induces Apoptosis in Umbilical Vein Endothelial Cells: Involvement of Annexin V," 205(2):1488-1493, Dec. 15, 1994.

Nilsson et al, "Immunization of mice and rabbits by intrasplenic deposition of nanogram quantities of protein attached to Sepharose beads or nitrocellulose paper strips," Journal of Immunological Methods 99:67-75, 1987.

Pengo, "Autoimmune Antiphospholipid Antibodies Are Directed against a Cryptic Epitope Expressed when β2-Glycoprotein I is Bound to a Suitable Surface," Thromb Haemost 73(1):29-34, 1995.

Pierangeli et al., "Are immunoglobulins with lupus anticoagulant activity specific for phospholipids?" British Journal of Haematology 85:124-132, 1993.

Piette et al., "Exclusion Criteria for Primary Antiphospholipid Syndrome," The Journal of Rheumatology 20:1802-1804.

Pittoni et al., "Apoptosis and Antiphospholipid Antibodies," Seminars in Arthritis and Rheumatism 28(3):163-178, Dec. 1998.

Ramirez, "Caracterizacion Fisica E Inmunologica de Arreglos Moleculares de No-Bicapa en Liposomas," Instituto Politecnico Nacional, Mexico, D.F., 1994.

Ramirez et al., "Determinación de Asociaciones Lipídicas de No-Bicapa en Liposomas y Membranas Celulares con Anticuerpos Monoclonales," Instituto Politecnico Nacional, Mexico, D.F., 1997.

Ramirez et al., Inducción y Caracterización de Anticuerpos Antifosfolipidos Obtenidos en Ratones BalB/c Tratados con Cloropromacina, Procainamida y Liposomas, Instituto Politecnico Nacional, Mexico, D.F., 1998.

Rauch et al., "Distinguishing Plasma Lupus Anticoagulants from Anti-Factor Antibodies Using Hexagona (II) Phase Phospholipids," Thrombosis and Haemostasis 62(3):892-896, 1989.

Rauch et al., "Inhibition of Lupus Anticoagulant Activity by Hexagonal Phase Phosphatidylethanolamine in the Presence of Prothrombin," Thromb Haemost 80:936-41, 1998.

Roubey et al., "'Anticardiolipin' Autoantibodies Recognize $\beta_2$-Glycoprotein I in the Absence of Phospholipid," Journal of Immunology pp. 954-960, 1995.

Schuber, "Influence of polyamines on membrane functions," Biochem. J. 260:1-10, 1989.

Shi et al., $\beta_2$-Glycoprotein I Is a Requirement for Anticardiolipin Antibodies Binding to Activated Platelets: Differences With Lupus Anticoagulants, Blood 81(5):1255-1262, Mar. 1, 1993.

Shoenfeld et al., "Lessons from experimental APS models," Lupus 7 (Suppl. 2):S158-S161, 1998.

Sugi et al., "Autoantibodies to Phosphatidylethanolamine (PE) Recognize a Kininogen-PE Complex," Blood 86(8):3083-9, Oct. 15, 1995.

Tan et al., "The 1982 Revised Criteria for the Classification of Systemic Lupus Erythematosus," Arthritis Rhem 25(11):1271-1277, Nov. 1982.

Tincani et al., "Animal Models of the Antiphospholipid Syndrome," The Antiphospholipid Syndrome, Chapter 6, pp. 71-82, ed. by Asherson et al., CRC Press, Boca Raton, 1996.

Baeza et al., "Antibodies to Non-Bilayer Phospholipid Arrangements Induce a Murine Autoimmune Disease Resembling Human Lupus," Eur. J. Immunol., 34(2):576-86, 2004.

Campos et al., "Determination of Non-Bilayer Phospholipid Arrangements and Their Antibodies in Placentae and Sera of Patients with Hypertensive Disorders of Pregnancy," Placenta, 27(2-3):215-24, 2006.

Bailey et al., "Liposome Fusion," Current Topics in Membranes, 44:359-373, 1997.

Cullis et al., "Phospholipids and Membrane Transport," Can. J. Biochem., 58:1091-1100, 1980.

de Kruijff, Ben, "Polymorphic Regulation of Membrane Lipid Composition," Nature, 329:587-588, 1987.

de Kruijff, Ben, "Lipids Beyond the Bilayer," Nature, 386:129-130, 1997.

Ellens et al., "Membrane Fusion and Inverted Phases," Biochemistry, 28:3692-3703, 1989.

Galli M., "Antiphospholipid Syndrome: Association Between Laboratory Tests and Clinical Practice," Pathophysiol Haemost Thromb, 33:249-255, 2003/2004.

Hanly J.G., "Antiphospholipid Syndrome: An Overview," CMAJ, 168(13):1675-1682, 2003.

Levine et al., "The Antiphospholipid Syndrome", N Engl J. Med., 346(10):752-763, 2002.

Lockshin, M.D., "Update on Antiphospholipid Syndrome," Bulletin of the NYU Hospital for Joint Diseases, 64(1&2):57-59, 2006.

Miyakis et al., "International Consensus Statement on an Update of the Classification Criteria for Definite Antiphospholipid Syndrome (APS)," J Thrombosis and Haemostasis, 4:295-306, 2006.

Verkleij et al., "Divalent Cations and Chlorpromazine Can Induce Non-Bilayer Structures in Phosphatidic Acid-Containing Model Membranes," Biochemica et Biophysica Acta, 684:255-262, 1982.

Verkleij et al., "The Lipidic Particle as an Intermediate Structure in Membrane Fusion Processes and Bilayer to Hexagonal H Transitions," Biochemica et Biophysica Acta, 600:620-624, 1980.

\* cited by examiner

Phosphorylcholine  Phosphorylserine  Phosphorylethanolamine

Glycerolphosphorylcholine  Glycerolphosphorylserine

METHOD FOR ANTIPHOSPHOLIPID SYNDROME

CROSS-REFERENCE TO RELATED APPLICATIONS

This application is a divisional of U.S. application Ser. No. 09/632,735, filed Aug. 4, 2000 now U.S. Pat. No. 6,777,193.

FIELD OF THE INVENTION

The present invention relates to obtaining antibodies that recognize lipids and more particularly, relates to methods for obtaining antibodies against lipidic structures that are different from the lipidic bilayer, and to the use of these antibodies in the diagnosis and/or treatment of diseases associated with the antiphospholipid syndrome; as well as for the determination of physiological states of the cell.

BACKGROUND OF THE INVENTION

Considering the state of the art, there are different studies which evidence the existence of antibodies that recognize lipids. For example, they have been detected in the serum of patients with antiphospholipid syndrome, as was described by Asherson et al. in their book "The antiphospholipid syndrome" in 1996 (*CRC Press*, Boca Raton). In the same way, antiphospholipid antibodies have been obtained from animals that were experimentally treated with lipids by active immunization, in accordance with Alving in 1992 (*Biochim. Biophys. Acta* 1113:307-322) and in animals that received antiphospholipid antibodies by passive immunization, as Tincani and Shoenfeld described in 1996 in the above mentioned book.

Anti-lipid antibodies have been classified into two major subgroups based on the method used for their determination. These groups are anti-cardiolipin antibodies and anticoagulant antibodies (Guglielmone y Fernandez, 1998, J. Rheumatol. 26:86-90).

Anti-cardiolipin antibodies are determined by methods using cardiolipin immobilized in a solid phase. Harris et al. in 1985 (Clin. Rheum. Dis. 11:591-609) described enzyme-linked immunosorbent assays and radioimmunoassays, better known by their respective abbreviations as ELISA and RIA. These have been broadly used in the above mentioned technique.

Anticoagulant antibodies are detected by measuring the prolongation in the coagulation time of plasma samples in vitro, according with Bevers et al. 1991 (Thromb. Haemost. 66:629-632). Some of these methods are: activated partial thromboplastin time (APTT), dilute Russell's viper venom time (dRVVT), protein C, and protein S, among others. In these methods, anticoagulant antibodies are bound to phosphatidylethanolamine or to phosphatidylserine, which are intermediary factors in the blood coagulation cascade, and when the concentration of these lipids decrease due to the immune reaction, the coagulation time is prolonged.

Anti-cardiolipin antibodies have the disadvantage of producing cross-reactions with other anionic lipids such as phosphatidylserine and phosphatidylglycerol. Due to their lack of specificity for a certain type of lipid, the above mentioned antibodies are generally known as antiphospholipid antibodies.

In addition, antibodies against phosphatidylethanolamine have been detected in the sera of patients with antiphospholipid syndrome. Also, antibodies against phosphatidylcholine are detected in patients with hemolytic anemia, as was described by Sugi and McIntyre (Blood 86:3083-3089) and Arvieux et al. (Thromb. Haemost. 74:1120-1125), respectively, in 1995.

On the other hand, some studies have demonstrated that the binding of antiphospholipid antibodies to the lipidic antigen increases in the presence of a plasma protein. For example, in 1990, McNeil et al., determined that the binding of antibodies to cardiolipin was markedly enhanced by the plasma protein $b_2$-glycoprotein I or apoprotein H (Proc. Nat. Acad. Sci. USA 87:4120-4124). Additionally, some anti-cardiolipin antibodies are bound directly to $b_2$-glycoprotein I, as was described by Roubey et al. in 1995 (J. Immunol. 154:954-960). These findings suggest that the anti-cardiolipin antibodies may recognize either a cryptic epitope on $b_2$-glycoprotein I exposed on the complex of $b_2$-glycoprotein I-cardiolipin, or $b_2$-glycoprotein I alone but with a very low affinity towards the glycoprotein, as was described by Pengo et al. (1995, Thromb. Haemost. 73:29-34).

In accordance with these studies, it may be concluded that the binding of antiphospholipid antibodies to lipidic antigens is also associated with proteins. Sugi and McIntyre (op. cit., 1995) found that proteins called kininogens are involved in the binding of antibodies to phosphatidylethanolamine, whereas proteins that are bound to phosphatidylserine, such as prothrombin, protein C, protein S and annexin V, have been implicated in the binding of anticoagulant antibodies to phosphatidylserine, according to the studies in 1994 by Nakamura et al. (Biochim. Biophys. Res. Commun. 205:1488-1493) and by Roubey (Blood 84:2854-2867).

These studies indicate that the antigen of some antiphospholipid antibodies is really a complex formed by phospholipids and specific plasma proteins, but these proteins differ from those required for reactivity of antiphospholipid antibodies with cardiolipin. Nevertheless, in other studies, antiphospholipid antibodies that bind directly to the phospholipid have been identified, for example anti-cardiolipin antibodies that do not require $b_2$-glycoprotein I. Such studies were carried out by McNeil et al. in 1989 (Br. J. Haematol. 73:506-513) and by Pengo and Basiolo in 1993 (Thromb. Res. 72:423-430).

On the other hand, some anti-cardiolipin antibodies, purified by affinity chromatography, do not show anticoagulant activity (McNeil et al., op. cit., 1989; Shi et al., 1993, Blood 81:1255-1262). However, other studies demonstrated that anti-cardiolipin and anticoagulant antibodies were removed by adsorption with cardiolipin (Pengo and Biasiolo, op. cit., 1993; Pierangeli et al. 1993, Br. J. Haematol. 85:124-132).

Additionally, studies in experimental animals, treated by passive or active immunization, employed methods for the detection of antiphospholipid antibodies which are the same as those described for the detection of human antiphospholipid antibodies. Furthermore, in these animal models, the different organs and tissues were analyzed by anatomical and histopathological studies, by immunofluorescent studies, and even by fetal resorption analysis in which the produced lesions in fetuses and placentas of the female animal models were also analyzed. These studies were performed by Tincani and Shoenfeld (op. cit. 1996) and by Shoenfeld and Ziporen (Lupus 7:S158-S161, 1998).

The previously mentioned studies show that the antiphospholipid antibodies described in human patients and in animal models have a broad specificity toward lipidic antigens. This broad specificity of the antibodies may be attributed, among other causes, to the lack of specificity of the methods used for the detection of the above described antibodies.

Such methods do not consider the chemical structure and the molecular association of lipidic antigens, as well as the chemical properties that the lipidic antigens have in nature. As a consequence, those methods use lipidic antigens where phospholipids are bound to artificial solid supports, such as in the ELISA and RIA methods, or they are in a molecular association that is not completely characterized, like in tests where the prolongation in coagulation time is detected.

There are only a few studies in which the molecular structure of the phospholipid employed as antigen has been considered, for example, the reports of Rauch et al. in 1989 and in 1998 (Thromb. Haemost. 62:892-896 and Thromb. Haemost. 80:936-941, respectively) and of Berard et al. (J. Lab. Clin. Med., 1993, 122:601-605). In these reports, the authors demonstrated that the anticoagulant activity of sera from some patients with systemic lupus erythematosus is inhibited by phosphatidylethanolamine which is associated in a hexagonal tubular II phase. This inhibition was not observed when the phospholipid was in a bilayer phase. However, the properties of the cellular membrane can not be related to the tubular association of phospholipids because this tubular lipidic association is practically incompatible with the vesicular structure of the cellular membrane, as different authors have established. In other words, in the lipidic antigens used in these studies, the phospholipids are in molecular arrangements that do not correspond to the molecular arrangements present in the cellular membrane.

Additionally, it is well known that the molecular structure of the plasma membrane of mammalian cells is an associated heteropolymer formed by phospholipids, glycolipids, cholesterol, proteins and glycoproteins, where the lipids are mainly in a bilayer molecular arrangement. Nevertheless, it is also known that lipids may have molecular arrangements different from a bilayer and that such arrangements depend on the molecular geometry of the lipids and the surrounding conditions.

Cylindrical shaped lipids, such as phosphatidate, phosphatidylglycerol, phosphatidylinositol, phosphatidyl-choline, phosphatidylserine, cardiolipin, sphingomyelin and diglucosyldiacylglycerides, are associated in closed bilayers, or liposomes in aqueous media. Cylindrical lipids constitute from 60 to 70% of membrane lipids.

On the other hand, the conic shaped lipids such as phosphatidylethanolamine, monoglucosyldiacylglycerides, and diacylglycerols, as well as the above mentioned lipids phosphatidate, cardiolipin, phosphatidylserine, and phosphatidylglycerol when in the presence of divalent cations, are assembled in the molecular phase known as hexagonal II (HII), which corresponds to tubular cylinders packed hexagonally. Inverted cone shaped lipids, such as lysophospholipids and gangliosides, are associated in micelles. Conic and inverted conic shaped lipids represent from 30 to 40% of membrane lipids.

Lipidic arrangements in hexagonal II or micellar phases, as well as any other structural arrangement of lipids that does not form a bilayer but is immersed in a bilayer, are, for the purposes of this invention, lipidic structures different from the lipidic bilayer, or lipidic particles, independent of the kind of lipids that are forming these structures.

In the same way, it is known that in the presence of divalent cations, drugs like chlorpromazine and procainamide, nonpolar peptides, proteins such as the protein of the bacteriophage M13, cholesterol, lanthanum ions, as well as with changes in temperature and pH, the conic lipids form molecular arrangements different from a lipidic bilayer. These lipidic arrangements are of transient nature because when the concentration of the compounds that induced their formation diminishes or when the temperature or the pH changes again, the conic shaped lipids return to the bilayer arrangement as was described by Cullis et al., in 1991 (Membrane Fusion. Marcel Dekker, New York), by Baeza et al. in 1995 (Biochem. Cell Biol. 73:289-297) and Aguilar et al., in 1999 (J. Biol. Chem. 274:25193-25196). Lipidic bilayer molecular arrangements are observed as a smooth surface by cryofracture analysis.

Lipids in general are molecules with low immunogenicity, and of the two molecular arrangements that lipids may adopt in cellular membranes, it is considered that the lipidic bilayer is less immunogenic because it is the arrangement that mainly constitutes the matrix of all cellular membranes.

However, it is known that lipidic structures different from the bilayer, which are stabilized by divalent cations and are observed as protuberances on the smooth surface of the bilayer by cryofracture analysis, induce the formation of antibodies that recognize lipids that are associated in lipidic particles and do not react with lipids associated in a bilayer.

In connection with the above-mentioned studies, Baeza and their collaborators in 1995 (op. cit.) reported the production of liposomes having lipid molecular arrangements different from a bilayer, as well as the antigenic activity of these molecular arrangements, because they were able to obtain polyclonal antibodies to them. By means of cytofluorometric analysis of the immune reaction they were also able to identify the presence of lipidic structures in the liposomes described, using them to obtain anti-lipidic particles polyclonal antibodies in mice sera.

To do this, mice were immunized by introducing artificially formed lipidic particles, which when present in excess, caused the wanted immune reaction. Until now, it was believed that molecular arrangements different from a bilayer, lipidic particles, would be also poorly immunogenic when they are present in nature, for example in human and animal cells, because lipidic particles are transient and therefore would not be detected by immune systems.

Additionally, from analysis of the above mentioned studies, one can observe that cardiolipin is the only lipid that has been able to react with antibodies present in patients with antiphospholipid syndrome or associated illnesses, and that the other phospholipids usually present in the cellular membrane generally must be associated with proteins to react with the antibodies from these patients, or must be associated in a molecular arrangement incompatible with the molecular structure of the cellular membrane; with the exception of the studies of Baeza and their collaborators (op. cit. 1995) on anti-lipidic particle antibodies which react with a lipidic molecular arrangement similar to the one that has been described in cellular membranes.

In this respect, the presence in the sera of patients with antiphospholipid syndrome anti-cardiolipin antibodies, a mitochondrial lipid, anti-nuclear antibodies and anti-DNA antibodies, indicates the existence of previous events that caused immunologic damage to cellular membranes, with the disruption of the cells and presentation of intracellular components to the immunologic system, causing the corresponding immunologic reaction that contributes to the development of the syndrome. However, up to now there have not been studies which allow one to determine the events that cause the disruption of the cellular membrane. In other words, with the existent knowledge so far, it is impossible to detect anti-cardiolipin antibodies, anti-nuclear or even anti-DNA antibodies before damage has been caused to the cell, impeding an early diagnosis and treatment of the illnesses associated with the syndrome.

Additionally, in the Doctoral Thesis presented by Leopoldo Aguilar Dec. 17, 1997 (Determination of non-bilayer lipidic arrangements in liposomes and cellular membranes with monoclonal antibodies", Doctoral Thesis, National School of Biological Sciences, National Polytechnic Institute, México) 5 sera from patients with primary antiphospholipid syndrome and 5 sera from patients with systemic lupus erythematosus were analyzed. The illnesses were corroborated by clinical characteristics that the patients presented and by means of the detection of anti-cardiolipin antibodies and of anti-nuclear antibodies, the latter in the case of the sick persons with lupus. The analyzed sera from all patients also contained anti-lipidic particles antibodies, detected according to the techniques of liposomal-ELISA and of liposomal cytofluorometry as described in the above mentioned Thesis.

This discovery, however, does not show any advantage for the early detection of the illnesses, since the presence of the antiphospholipid antibodies and of the anti-lipidic particles antibodies in those patients can be explained according with two hypothesis.

The first hypothesis assumes that an unknown factor causes the destruction of the cellular membrane, which promotes the formation of lipidic particles from membrane lipids that enter in contact with the immunologic system together with the intracellular components, consequently simultaneously forming anti-lipidic particle antibodies and anti-cardiolipin and anti-nuclear antibodies.

The second hypothesis assumes that lipidic particles are formed in the cellular membrane before its destruction, and the anti-lipidic particles antibodies formed destroy the membrane, exposing the intracellular components to the immunologic system and causing later formation of anti-cardiolipin and anti-nuclear antibodies.

This second hypothesis was proposed in the Master Thesis presented by Monica Lara on Aug. 20, 1999 ("Detection of anti-lipidic particles antibodies in patients with the anti-phospholipid syndrome," Master Thesis, Escuela Nacional de Ciencias Biologicas [National School of Biological Sciences], Instituto Politécnico Nacional [National Polytechnic Institute], Mexico.

So far, neither of the two hypothesis has been demonstrated, which is of supreme importance for the treatment of the illnesses, since should the second hypothesis be proved, it would be possible to detect the above-mentioned illnesses in their early stages, and also prevention, cure or patient improvement from such illnesses would be possible.

Based on the above-mentioned hypothesis, it has been aimed to avoid the inconveniences of methods using induction and detection of antiphospholipid antibodies caused by the structure and molecular association of the antigens by using lipidic antigens with a structure and molecular association similar to that found in patients with illnesses associated with antiphospholipids antibodies. These novel lipidic antigens have been used for the induction and detection of anti-lipidic particle antibodies that allow an early diagnosis of these illnesses, as well as for the determination of physiologic states of the cell such as apoptosis (programmed cellular death) (Pittoni and Isenberg, 1998, Semin. Arthritis. Rheum. 28:163-178) and those associated with the cellular cycle (Go, G1, G2 and M) among others.

OBJECTS OF THE INVENTION

Keeping in mind deficiencies in the structure and in the molecular association of the antigens used in the techniques of induction and detection of antiphospholipid antibodies in the methods of the prior techniques, one of the objectives of the present invention is to use lipidic antigens with a structure and molecular association similar to the one that is present in patients with illnesses associated with antiphospholipid antibodies, with the purpose of providing a method for the detection of anti-lipidic particle antibodies.

It is another objective of the present invention to provide a diagnostic method which uses monoclonal antibodies specific to lipidic antigens that respond in the same way as the anti-lipidic particle antibodies present in sera from patients with diverse illnesses associated with antiphospholipid antibodies, with the purpose of designing a strategy for treatment of these patients for such illnesses.

It is an additional objective of the present invention to provide a kit or diagnosis set for the detection of anti-lipidic particle antibodies in early stages of illnesses that present such antibodies in animals and in humans.

It is another objective of the present invention to provide a kit or diagnosis set for the detection of lipidic particles in the membranes of the cells of ill entities, human or animal, that present anti-lipidic particle antibodies.

It is still another objective of the present invention to provide a method for the prevention, cure or patient improvement of such illnesses by means of inhibiting or blocking of anti-lipidic particles antibodies.

Yet another objective of the present invention consists of providing a method for the prevention, cure or patient's improvement of such illnesses by means of stabilizing cellular membranes to impede the formation of lipidic particles and therefore the later formation of anti-lipidic particle antibodies.

An additional objective of the present invention consists of providing methods and corresponding kits for the detection of different physiologic states that can present in cells, which can lead to the prevention of illnesses related to antiphospholipid antibodies.

DETAILED DESCRIPTION OF THE PREFERRED EMBODIMENTS

Figure 1:
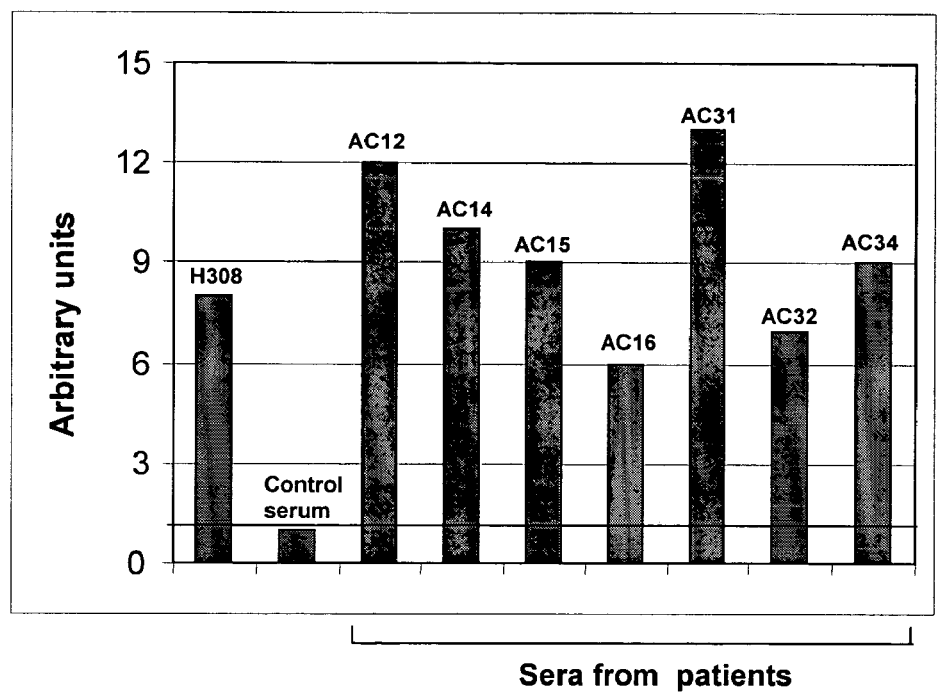
FIG. 1 shows analysis by the liposomal-ELISA method of the reaction between control sera from human healthy blood donors or sera from patients with antiphospholipid syndrome and liposomal antigen made from egg-yolk phosphatidylcholine:phosphatidate (PC:PA) (2:1 mole ratio) bearing lipidic particles induced by calcium. Furthermore, the reaction of H308 monoclonal antibody with these antigens is also indicated.

Despite the transitory nature of lipidic particles in active cellular membranes, it has been found surprisingly that sera from patients who present illnesses associated with antiphospholipid syndrome react with C5337 human pancreas cancer cells, which is indicative of a prolonged presence of lipidic particles in cellular membranes of these patients.

Equally, when an antigen that contains lipidic particles was administered to BALB/c mice it has been found surprisingly that these mice developed alopecia and lesions on the face in the form of butterfly wings similar to those described in some human autoimmune illnesses, as well as deposits of immune complexes and pathological alterations in different organs. Additionally, it has been also found that these mice firstly developed anti-lipidic particle antibodies and subsequently anti-cardiolipin antibodies, lupus anticoagulant and anti-nuclear antibodies, which confirms that anti-lipidic particle antibodies constitute the first stage in the development of illnesses associated with antiphospholipid antibodies.

According to the above-mentioned experiments, the presence of anti-lipidic particles antibodies in one of the first stages of the illness indicates that one of the first events that occurs in antiphospholipid syndrome is the formation of anti-lipidic particle antibodies. These antibodies, when reacting with lipidic particles in cellular membranes cause damage in these membranes, and finally cell disruption and the presentation of intracellular components to the immune system; which explains the subsequent presence of anti-cardiolipin antibodies (since cardiolipin is a mitochondrial lipid) and of anti-nuclear and anti-DNA antibodies, which have been reported as present in these illnesses in humans.

For the purposes of the present invention, "illness associated with antiphospholipid antibodies" is understood as any illness that presents antiphospholipid antibodies in any development step. Some of such illnesses are mentioned next, in an enunciative fashion, but not limitative: primary or secondary antiphospholipid syndrome (the latter associated with autoimmune illnesses such as vasculitis, rheumatoid arthritis and systemic lupus erythematosus); illnesses that cause an increase in cellular division (which can be neoplasias such as carcinoma of the liver or ovary, lymphomas, leukemias or myeloproliferative disorders); viral infections (such as infectious mononucleosis and acquired immunodeficiency syndrome); illnesses caused by bacteria (such as syphilis); and illnesses caused by protozoa (such as malaria). Additionally, the presence of antiphospholipid antibodies has been correlated with myocardial infarction and senility.

Therefore, an aspect of the present invention is to develop a diagnostic method for determining if an individual who has clinical characteristics of primary antiphospholipid syndrome (Table 1), or one of the illnesses associated with secondary antiphospholipid syndrome (Table 1) and who does not yet present anti-cardiolipin antibodies, lupus anti-coagulant, anti-DNA or anti-nuclear antibodies, does have an illness associated with the presence of antiphospholipid antibodies; where such method comprises the steps of detecting, in a direct or indirect fashion, the presence or absence of lipidic particles in a sample from said individual, and to observe whether lipidic particles are detected or not, where the presence of said lipidic particles indicates the development of an illness associated with the presence of antiphospholipid antibodies in said individual.

In a preferred embodiment, the detection of lipidic particles is carried out in an indirect fashion by reacting an antigen containing lipidic particles with the serum of the subject with the purpose of determining if anti-lipidic particle antibodies exist in this serum, such a determination being carried out preferably by means of at least one technique selected from the group consisting of ELISA, cytofluorometry, and immunofluorescence.

In a specific embodiment, the antigen containing lipidic particles is selected from neoplastic cells and liposomes where the liposomes are formed from at least one lipid that is susceptible to changing its molecular geometry due to changes in temperature, presence of divalent cations, and/or drugs. This lipid preferably is selected from phosphatidate; cardiolipin; phosphatidylglycerol; phosphatidylinositol; diacylglycerol; sphingomyelin; phosphatidylserine; monoglucosyldiacylglyceride or phosphatidylethanolamine. In a favorite modality, the lipid is found in abundance in cellular membranes.

In a specific embodiment, the lipids used to form liposomes are selected due to their availability in cellular membranes and due to anti-lipid antibodies against them having been detected in humans, using preferably one lipid with a cylindrical molecular shape in combination with one lipid with a conical molecular shape in a mole ratio between 1:1 to 4:1. In an additional modality, a combination of phosphatidylcholine with phosphatidate from egg yolk in a 2:1 molar ratio is used.

In another additional embodiment, at least an anti-lipidic particle polyclonal or monoclonal antibody is made to react with neoplastic cells or liposomal antigens to confirm the presence or not of anti-lipidic particle antibodies in the individual serum.

In another preferred embodiment, detection of lipidic particles is carried out in a direct fashion by reacting cells from the subject with at least an anti-lipidic particle polyclonal or monoclonal antibody, preferably by means of the use of at least one technique selected from the group consisting of immunofluorescence, cytofluorometry and ELISA.

In an additional embodiment, in addition to cells of the subjects, anti-lipidic particle antibodies are reacted with at least an antigen that contains lipidic particles, preferably selected from neoplastic cells and liposomes having at least one lipid susceptible to changing its molecular geometry due to changes in temperature, presence of divalent cations, and/or drugs, this lipid preferably is selected from phosphatidate; cardiolipin; phosphatidylglycerol; phosphatidylinositol; diacylglycerol; sphingomyelin; phosphatidyl-serine; monoglucosyldiacylglyceride or phosphatidylethanolamine In a specific embodiment, the lipids used to form liposomes are selected due to their availability in cellular membranes and due to anti-lipid antibodies against them having been detected in humans, using preferably a cylindrical lipid in combination with a conical lipid in a mole ratio between 1:1 to 4:1. In an additional modality, a combination of phosphatidylcholine with phosphatidate from egg yolk in a 2:1 molar ratio is used.

To obtain the liposomes that are used in several modalities of the present invention, the reverse phase evaporation method is preferably used, as modified by Baeza and collaborators in 1994 (J. Mol. Evol., 39:560-568), and subsequently the liposomes are treated with a lipidic particle-inducer agent, preferably selected from divalent cations and drugs, preferably those that produce lupus induced by drugs in humans, or combinations of these; where the procedure to form lipidic particles preferably is by means of incubation of liposomes with an effective quantity of the lipidic particle-inducer agent at a temperature between 25 to 40° C., this effective quantity being preferably in a mole ratio (lipids:lipidic particle-inducer agent) from 1:0.01 up to 1:300.

On the other hand, anti-lipidic particle polyclonal antibodies useful for diverse modalities of the present invention are obtained by any known mouse immunization method, using an antigen that contains lipidic particles, preferably by means of a immunization procedure of the type described by Baeza and collaborators (op. cit., 1995), which comprises:

A) A first step of mice immunization using intrasplenic injection of an effective dose of liposomes obtained from lipids against which anti-lipid antibodies have been detected in humans, where these liposomes contain lipidic particles in their surface.

B) A second step of mice immunization using intraperitoneal injection of the same liposomes and with the same doses used in the first immunization step.

When concluding these steps, immunized mice produce anti-lipidic particle polyclonal antibodies which can be detected by the liposomal-ELISA method and/or the liposomal cytofluorometry method.

In a specific embodiment, the effective liposome doses were from 50 to 200 mg, preferably incubated in a solution from 0.1 to 10 mM of $CaCl_2$, $MnCl_2$, chlorpromazine, procainamide or combinations of these in the presence of a buffer solution with a pH between 7.0 to 7.4.

In an additional embodiment, in the first immunization step it is necessary to administer liposomes at least 2 times by intrasplenic injection with intervals of 1 week, and in the second immunization step it is necessary to introduce liposomes by intraperitoneal injection at least 4 times with intervals of 2 weeks, according to the method described by Nilsson et al. in 1987 (J. Immunol. Methods 99:67-75) and modified by Aguilar in 1994 ("Physical and immunologic characterization of non-bilayer molecular arrangements in liposomes", Master Thesis, National School of Biological Sciences, National Polytechnic Institute, México).

In another additional embodiment, mice used for immunization were selected from a syngeneic strain, using preferably 2-month old BALB/c female mice.

Starting with the immunized mice, it is possible to obtain monoclonal antibodies by means of any well-known method, preferably by obtaining a hybridoma. In a specific modality, the hybridoma was obtained according with the following steps:

A) Mice that were immunized by intrasplenic and intraperitoneal injections received a third immunization by intravenous administration of the liposomes at doses used for the first and second immunization steps.

B) A fusion step of immunized mouse spleen cells with myeloma mouse cells that do not secrete gamma chains nor kappa chains. This fusion was carried out at least 4 days after the intravenous immunization to obtain at least a hybridoma producing an anti-lipidic particle monoclonal antibody.

C) A step of hybridomas selection, in which the hybridoma is selected from those which produce detectable immunoreaction, using the liposomal-ELISA method and/or the cytofluorometry method to detect the anti-lipidic particle antibodies.

In a specific embodiment, the effective liposome doses were between 50 to 200 mg, preferably incubated with a solution from 0.1 to 10 mM of $CaCl_2$, $MnCl_2$, chlorpromazine, procainamide or combinations of these in the presence of a buffer solution with a pH between 7.0 to 7.4.

In an additional embodiment, the first immunization step includes the administration of liposomes at least 2 times by intrasplenic injection with intervals of 1 week, and the second immunization step includes the introduction of liposomes by intraperitoneal injection at least 4 times with intervals of 2 weeks, using the method described by Nilsson et al. (op. cit., 1987) as modified by Aguilar (op. cit., 1994).

In another additional embodiment, mice used for immunization were selected from a syngeneic strain, preferably using 2-month old BALB/c female mice.

In a preferred embodiment of the present invention, immunized mouse spleen cells are obtained according to the procedure described by Aguilar (op. cit., 1997), by dispersion of the mouse spleen in an appropriate cellular culture medium, preferably incomplete DMEM medium or RPMI medium with added glutamine (200 mM) and glycine (100 mM), followed by diverse purification steps and erythrocyte lysis, preferably with ammonium chloride, which generally only disrupts erythrocytes without affecting lymphocytes or leukocytes.

Cells of the P3X63Ag8U.1 mouse myeloma cell line obtained by Yeltan (Curr. Top. Microbiol. Immunol., 1978, 81:1-7) are preferably used. This cell line is derived from the cell line obtained by Kohler and Milstein (Nature, 1975, 256:495-497) from BALB/c female mice MOPC21 myeloma.

Regarding the method used for cellular fusion, preferably the one described by Aguilar (op. cit., 1997) is used. This method consists of using immunized mouse spleen and myeloma cells with a viability higher than 95%, which are centrifuged and mixed in a cellular proportion of 1:1, and subsequently subjected to diverse washing steps and cultured in cellular culture microtiter plates previously seeded with macrophages.

With respect to the methods used for detection of anti-lipidic particle antibodies in patient sera using antigens that contain lipidic particles, or for detection of lipidic particles in cells from patients using anti-lipidic particle antibodies, the favorite techniques will be next described.

It is important to point out that in the description of these techniques the term "antibody porter" refers to any fluid which can contain anti-lipidic particle antibodies, therefore it can be plasma or serum of human or animal origin, a solution or a suspension; while the term "antigen" refers to those structures which can contain lipidic particles, such as liposomes or cells.

Additionally, it is also important to point out that in a specific modality of the present invention, before starting to use any detection method, inactivation of the serum or of the plasma is carried out by increasing their temperature, preferably subjecting serum or plasma to temperatures between 50 to 60° C. for 0.25 to 1 h.

On the other hand, the liposomal-ELISA method (Aguilar, op. cit., 1994; 1997; Aguilar et al., op. cit., 1999), as its name indicates, is applicable in those cases in which the antigen is a liposome, independent of the origin of the antibody porter, and comprises the following steps:

A) A first step of addition and incubation, in which an effective quantity of an antigen suspension is added to each one of the wells of the ELISA microtiter plate. This microtiter plate is selected from those with a high lipidic antigen binding property and said microtiter plate is incubated between 25 to 30° C. for 0.25 to 2 h.

B) A second step of addition and incubation, in which an effective quantity of a blocking solution is added to each one of the wells of the ELISA microtiter plate with a high lipidic antigen binding property, and said microtiter plate is incubated at a temperature between 25 to 30° C. for 0.25 to 2 h.

C) A step of elimination of blocking solution, preferably by suction, with caution to avoid the microtiter plate becoming dry when blocking solution is removed, because liposomal antigens can be damaged.

D) A third step of addition and incubation, in which an effective quantity of the antibody porter is quickly added, to avoid the microtiter plate becoming dry, to each one of the wells, using an antibody porter dilution from 1:5 to 1:1000 in blocking solution; and said microtiter plate is incubated for 0.25 to 2 h at a temperature between 25 to 30° C.

E) A first step of washing, in which the microtiter plate is washed with the blocking solution, preferably repeating 4 times, avoiding the microtiter plate becoming dry when removing the blocking solution.

F) A fourth step of addition and incubation, in which an effective quantity of a secondary antibody is added to each one of the wells of microtiter plate. This plate is incubated in the darkness for 0.25 to 2 h at a temperature between 25 to 30° C. The secondary antibody is selected preferably from antibodies from a different species from that of the antibody porter and can be anti-IgG, IgA or IgM Fc (human or the animal in study), or anti-IgM or IgG Fc antibodies depending on the nature of the monoclonal antibody when this is the antibody porter. Secondary antibody is used at a final dilution in blocking solution between 1:000 and 1:3500 and is conjugated to an enzyme preferably to peroxidase.

G) A second step of washing, in which the microtiter plate is washed with blocking solution, preferably repeating 4 times and avoiding the microtiter plate becoming dry when removing the blocking solution.

H) A fifth step of addition and incubation, in which an effective quantity of peroxidase substrate is added to each one of the wells and said microtiter plate is incubated for 0.1 to 0.5 h at a temperature between 35 and 40° C., and the peroxidase reaction is stopped by adding an effective quantity of sulfuric acid.

I) A step of analysis, in which microtiter plate is analyzed in a reading device for ELISA, preferably at 492 nm.

In a specific embodiment, the antigen suspension is obtained by suspending liposomes in a buffer solution at a pH between 7.0 to 7.4, at 1 to 5 mmole antigen per liter of buffer solution.

The blocking solution includes a buffer solution at pH between 7.0 to 7.4, and at least a solution with a high protein concentration, preferably gelatin at 0.4%, weight by volume, with or without an effective quantity of a lipidic particle-inducer agent, preferably with an effective quantity of the lipidic particle-inducer agent used to form the antigen.

In a preferred embodiment, the effective quantity of the antigen suspension in step A is 50 to 100 ml. The secondary antibody can be conjugated to the enzyme alkaline phosphatase instead of peroxidase, and in this case the corresponding alkaline phosphatase substrate is used.

The liposomal-ELISA method allows simultaneous determination of anti-lipidic particle antibodies in at least 40 serum samples, each one in duplicate, in a single microtiter plate, therefore this method can be easily applied to the diagnosis of illnesses where this type of antibodies are present.

On the other hand, the liposomal cytofluorometry method (Baeza and collaborators., op. cit., 1995), as its name indicates, is applicable in those cases in which the antigen is a liposome, independent of the origin of the antibody porter, and it includes the following steps:

A) A first step of addition and incubation, in which the antibody porter is added to the antigen suspension. This antibody porter is diluted from 1:5 to 1:1000 in a buffer solution at pH between 7.0 to 7.4, and the resulting mixture is incubated for 0.25 to 2 h at a temperature between 35 and 40° C.

B) A first step of washing, in which the antigen, bound to the antibody porter, is washed with a buffer solution at pH between 7.0 to 7.4, with or without an effective quantity of a lipidic particle-inducer agent, preferably with the same quantity and the same inducer agent used to obtain the antigen.

C) A step of recovery, in which the antigen bound to the antibody porter is recovered, preferably by centrifugation.

D) A second step of addition and incubation, in which an effective quantity of a secondary antibody is added to the antigen bound to the antibody porter. The resulting mixture is incubated for 0.25 to 2 h in darkness at a temperature between 35 to 40° C. The secondary antibody is selected preferably from antibodies from a different species from that of the antibody porter and can be anti-IgG, IgA or IgM Fc (human or the animal in study), or anti-IgM or IgG Fc antibodies depending on the nature of the monoclonal antibody when this is the antibody porter. Secondary antibody is used at a final dilution from 1:25 to 1:500 in a buffer solution at pH between 7.0 to 7.4, and is conjugated to a substance or fluorescent substrate, preferably fluorescein isothiocyanate (FITC).

E) A second step of washing, in which the antigen bound to the antibody porter and to the secondary antibody is washed with a buffer solution at pH between 7.0 to 7.4, with or without an effective quantity of a lipidic particle-inducer agent, preferably with the same quantity and the same inducer agent used to obtain the antigen.

F) A step of suspension and analysis, in which the antigen bound to the antibody porter and the secondary antibody is suspended in a transporting solution, selected preferably from FACS Flow (Beckton Dickinson Co.) and Haema Line 2 (Serotono-Baker Diagnostics, INC) at 1 to 5 mmole antigen per liter of solution; this solution being preferably filtered previously with a 0.22 μm pore diameter Millipore™ filter, the obtained mixture being analyzed in a flow cytometer, preferably with a single 488 nm argon laser beam.

In a preferred embodiment, the antigen suspension is obtained by suspending liposomes in a buffer solution at a pH between 7.0 to 7.4, at 1 to 5 mmole per liter of buffer solution. Furthermore, the fluorescent substrate can also be selected from the group consisting of phycoerythrin, Cy3 and Percp.

The liposomal cytofluorometry method has a sensitivity 10-fold higher than the liposomal-ELISA method in the detection of anti-lipidic particle antibodies. Therefore, this method must be applied when a doubtful result has been obtained with the liposomal-ELISA method. The cytofluorometry method also allows one to analyze the presence of lipidic particles in liposomal or cellular antigens, as well as to compare the different types of reactions of polyclonal or monoclonal antibodies with the lipidic particles of these antigens.

In another preferred embodiment of the cytofluorometry method, the suspension of the antigen can be from human or animal cells, and the suspension of the antigen is obtained by suspending the cells, preferably isolated erythrocytes, leukocytes and even platelets in a buffer solution at a pH between 7.0 to 7.4. With the exception of this difference regarding the antigen, the steps of this cytofluorometry method are as those described in subparagraph (A) to (F) for the liposomal cytofluorometry method in which liposomes are used as antigens.

Regarding cellular methods, the immunofluorescence method for cells, applicable when the antigen is a cell, comprises the following steps:

A) A step of cell culture, in which an effective quantity of the antigen, preferably $1 \times 10^6$ cells, is placed on a micro cover glass inside each well of a cell culture plate and is incubated under an atmosphere containing an effective $CO_2$ quantity at a temperature between 35 to 40° C. until cellular confluence reaches 90%.

B) A first step of washing, in which the antigen is washed with an appropriate cell culture medium, preferably repeating 2 times, with a phosphate buffer solution at a pH between 7.0 to 7.4, under sterile conditions. Avoiding the surface of cellular culture becoming dry when removing the phosphate buffer solution, which can damage cellular antigens.

C) A first step of addition and incubation, in which an effective quantity of an antibody porter is added to the cellular antigen, preferably 50 to 200 μl without dilution or with a maximum dilution of 1:1000 in an appropriate cell culture medium. Cellular antigen, treated with the antibody porter, are incubated under an atmosphere containing an effective $CO_2$ quantity for 0.25 to 2 h at a temperature between 35 to 40° C.

D) A second step of washing, in which the antigen bound to the antibody porter is washed with a phosphate buffer solution at pH between 7.0 to 7.4. Preferably repeating 3 times and avoiding the surface of the cellular culture becoming dry when removing the phosphate buffer solution.

E) A second step of addition and incubation, in which an effective quantity of a secondary antibody is added to the antigen bound to the antibody porter. The mixture obtained is incubated under an atmosphere containing an effective $CO_2$ quantity for 0.25 to 2 h at a temperature between 35 to 40° C. The secondary antibody is selected preferably from antibodies from a different species from that of the antibody porter and can be anti-IgG, IgA or IgM Fc (human or the animal in study), or anti-IgM or IgG Fc antibodies depending on the nature of the monoclonal antibody when this is the antibody porter. The secondary antibody is used at a final dilution from 1:25 to 1:500 in an appropriate cell culture medium and is conjugated to a substance or fluorescent substrate, preferably to FITC.

F) A third step of washing, in which the antigen bound to the antibody porter and to the secondary antibody is washed with a phosphate buffer solution at a pH between 7.0 to 7.4, preferably repeating 3 times and avoiding the surface of the cellular culture becoming dry when removing the phosphate buffer solution.

G) A step of analysis, in which a micro cover glass is mounted, preferably on a slide with a fluorescence protector such as VectaShield™, for observation in a confocal microscope or with epifluorescence and Nomarski optics.

In a specific embodiment, the effective quantity of $CO_2$ is attained with 1 to 10% in volume with respect to air, while the effective quantity of phosphate buffer solution is attained with 1 to 10 ml. The fluorescent substrate can also be selected from the group consisting of phycoerythrin, Cy3 and Percp.

In another preferred embodiment of the immunofluorescence method, microsections of an organ from humans or animals can be used as antigen, instead of a cell culture as described previously. With the exception of this difference regarding the antigen, the steps of this immuno-fluorescence method are as those described in subparagraphs (B) to (G) for the immunofluorescence method in which a cell culture is used as antigen.

Finally, the cellular-ELISA method includes the following steps:

A) A step of culture, in which an effective quantity of cellular antigen is added to each of the wells of a microtiter plate, preferably 1×10$^5$ cells, this antigen being cultured until confluence reaches 100%.

B) A first step of addition and incubation, in which an effective quantity of a blocking solution is added to each of the wells of microtiter plate, and said plate is incubated between 35 to 40° C. for 0.5 to 1 h.

C) A step of removal of blocking solution, avoiding the surface of the cellular culture becoming dry when removing the blocking solution, which can damage cellular antigens.

D) A second step of addition and incubation, in which an effective quantity of an antibody porter is added to each of the wells of microtiter plate in an antibody porter dilution from 1:5 to 1:1000 in blocking solution; said microtiter plate being incubated for 0.25 to 2.0 h at a temperature between 35 to 40° C. in presence of an effective quantity of $CO_2$.

E) A first step of washing, in which cell cultures are washed with the blocking solution, preferably repeating 3 times and avoiding the surface of the cellular culture becoming dry when removing the blocking solution.

F) A third step of addition and incubation, in which an effective quantity of a secondary antibody is added to each of the wells of microtiter plate. This plate is incubated for 0.25 to 2 h at a temperature between 35 to 40° C. in the presence of an effective quantity of $CO_2$. The secondary antibody is selected preferably from antibodies from a different species from that of the antibody porter and can be anti-IgG, IgA or IgM Fc (human or the animal in study), or anti-IgM or IgG Fc antibodies depending on the nature of the monoclonal antibody when this is the antibody porter. The secondary antibody is used at a final dilution from 1:1000 to 1:3500 in blocking solution and is conjugated to an enzyme, preferably peroxidase.

G) A second step of washing, in which microtiter plate is washed with the blocking solution, preferably repeating 3 times and avoiding the surface of the cellular culture becoming dry when removing the blocking solution.

H) A fourth step of addition and incubation, in which an effective quantity of peroxidase substrate is added to each of the wells of the microtiter plate, said plate being incubated for 0.1 to 0.5 h at a temperature between 35 to 40° C., and stopping the peroxidase reaction by means of an effective quantity of sulfuric acid.

I) A step of analysis, in which the microtiter plate is analyzed in a reading device for ELISA, preferably at 492 nm.

In a specific embodiment, the effective quantity of $CO_2$ is attained with 1 to 10% in volume with respect to air, while the effective quantity of phosphate buffer solution is attained with 1 to 10 ml.

The blocking solution includes a buffer solution at a pH between 7.0 to 7.4, and at least a solution with a high protein concentration, preferably fetal calf serum at 5%, volume by volume, with or without an effective quantity of a lipidic particle-inducer agent, selected preferably from solutions from 0.1 to 10 mM of $CaCl_2$, $MnCl_2$, chlorpromazine, procainamide or combinations of these.

On the other hand, in another specific modality of this method, the secondary antibody can be conjugated to the enzyme alkaline phosphatase, instead of peroxidase, in this case the corresponding alkaline phosphatase substrate is used.

Another aspect of the present invention is to develop an in vitro diagnostic instrument for illnesses associated with antiphospholipid antibodies, useful to carry out the method of the present invention. This diagnostic instrument includes at least an indicator reagent to detect the presence of lipidic particles or anti-lipidic particle antibodies in a sample from an individual having clinical characteristics of primary antiphospholipid syndrome (Table 1), or of the illnesses associated with secondary antiphospholipid syndrome (Table 1) and who does not yet present anti-cardiolipin antibodies, lupus anticoagulant, anti-DNA or anti-nuclear antibodies; media to allow the reaction of the sample with the indicator reagent; and, procedures to make this reaction evident.

In a preferred embodiment, the indicative reagent is selected from liposomes with lipidic particles in their surface, neoplastic cells, anti-lipidic particle polyclonal antibodies, and/or anti-lipidic particle monoclonal antibodies.

In another preferred embodiment, the sample is selected from cells and plasma or serum of the individual. Furthermore, the medium to allow the reaction includes at least a reaction regulating solution and at least a device to contain the reagent, the sample and the regulating solution.

The regulating solution is selected preferably from buffer solutions at a pH between 7.0 to 7.4, with or without a lipidic particle-inducer agent, and phosphate buffer solutions at a pH between 7.0 to 7.4, with or without a lipidic particle-inducer agent.

On the other hand, the device to keep the reagent, the sample and the regulating solution is selected preferably from tubes for centrifugation, microtiter plates containing micro cover glasses; ELISA microtiter plates with a high lipidic antigen binding property; and microtiter plates for cellular-ELISA. In the modality in which ELISA microtiter plates and/or cellular-ELISA microtiter plates are used, the diagnosis set also includes a blocking solution that includes a buffer solution at a pH between 7.0 to 7.4, a solution with a high protein concentration, and an effective quantity of a lipidic particle-inducer agent, the proteins preferably being selected from gelatin and fetal calf serum at a concentration of 0.4 to 5%, weight by volume, or volume by volume, respectively.

On the other hand, the procedures to detect the reaction are selected from fluorescent procedures and enzymatic procedures, preferably reactions of antibodies conjugated to a fluorochrome, preferably fluorescein isothiocyanate or conjugated to an enzyme, preferably peroxidase.

Regarding the individual sample, this is selected preferably from plasma or serum of the ill subject and cells from organs of the ill individual.

An additional aspect of the present invention consists of preventing or treating illnesses associated with antiphospholipid antibodies by administering a therapeutically effective quantity of a drug for inhibition or blocking the anti-lipidic particle antibodies from sick persons, or by administering a therapeutically effective quantity of a stabilizer drug to achieve stabilization of cellular membranes in sick persons. The above-mentioned processes are achieved in vitro by inhibiting or blocking the anti-lipidic particle antibodies from sick persons with phosphorylated haptens (which are chemical substances that are part of the polar region of the cellular membrane lipids) in a similar way to that demonstrated in the inhibition of H308 monoclonal antibody by phosphorylcholine and glycerolphosphoryl-choline haptens (Aguilar, op. cit. 1997).

Regarding the stabilization of cellular membranes, a therapeutically effective quantity of antimalaria drugs, which have also been used in the treatment of some illnesses of antiphospholipid syndrome, such as rheumatoid arthritis and systemic lupus erythematosus (Gibson et al., 1987, Br. J. Rheumatol. 26:279-285), is used. Among these drugs, it is possible to mention: chloroquine, hydroxichloroquine, amodiaquin, quinacrine or primaquine; or polyamines such as putrescine, spermidine or spermine; these polyamines are polycations which stabilize cellular membranes (Schuber, 1989, Biochem. J. 260:1-10). Both type of drugs avoid the formation of lipidic particles in membrane models such as liposomes or in cellular membranes, which avoids the subsequent binding of anti-lipidic particle antibodies, according with studies carry out by our investigation group.

When "a therapeutically effective quantity" of a drug with inhibitory properties is used in the present invention, it means a quantity of the inhibitor drug that when it is administered to an ill subject blocks anti-lipidic particle antibodies circulating in the blood stream of the subject under treatment. "A therapeutically effective quantity" of a stabilizer drug is a quantity of the stabilizer drug that when it is administered to an ill subject stabilizes cellular membranes in the individual under treatment, so that more anti-lipidic particle antibodies are no longer generated in this subject; or that the anti-lipidic particle antibodies present in the ill individual no longer react with cellular membranes because these membranes no longer present lipidic particles.

Studies on the inhibition of anti-lipidic particle antibodies were carried out using liposomes as antigens and the antigen-antibody reaction was analyzed by the liposomal-ELISA method, which includes the following steps:

A) A first step of addition and incubation, in which an effective quantity of an antigen suspension is added to each of the wells of the ELISA microtiter plate. This microtiter plate is selected from those with a high lipidic antigen binding property and said microtiter plate is incubated between 25 to 30° C. for 0.25 to 2 h.

B) A second step of addition and incubation, in which an effective quantity of a blocking solution is added to each of the wells of the ELISA microtiter plate with a high lipidic antigen binding property, and said microtiter plate is incubated at a temperature between 25 to 30° C. for 0.25 to 2 h.

C) A step of removing blocking solution, preferably by suction, avoiding the microtiter plate becoming dry when blocking solution is removed, because liposomal antigens can be damaged.

D) A step of inhibition of the antibody porter, in which the antibody porter is incubated with a chemical substance, or hapten, that will inhibit the active site that recognizes the antigen in the antibody porter.

E) A third step of addition and incubation, in which an effective quantity of the antibody porter inhibited by the hapten is added, quickly to avoid the microtiter plate becoming dry, to each of the wells using an antibody porter dilution from 1:5 to 1:1000 in blocking solution. This microtiter plate is incubated for 0.25 to 2 h at a temperature between 25 to 30° C.

F) A first step of washing, in which the microtiter plate is washed with the blocking solution, preferably repeating 4 times and avoiding the microtiter plate becoming dry when eliminating the blocking solution.

G) A fourth step of addition and incubation, in which an effective quantity of a secondary antibody is added to each of the wells of a microtiter plate. This plate is incubated in darkness for 0.25 to 2 h at a temperature between 25 to 30° C. The secondary antibody is selected preferably from antibodies from a different species from that of the antibody porter and can be anti-IgG, IgA or IgM Fc (human or the animal in study), or anti-IgM or IgG Fc antibodies depending on the nature of the monoclonal antibody when this is the antibody porter. The secondary antibody is used in a final dilution in blocking solution between 1:000 and 1:3500 and is conjugated to an enzyme, preferably peroxidase.

H) A second step of washing, in which the microtiter plate is washed with the blocking solution, preferably repeating 4 times and avoiding the microtiter plate becoming dry when removing the blocking solution.

I) A fifth step of addition and incubation, in which an effective quantity of the peroxidase substrate is added to each of the wells and this microtiter plate is incubated for 0.1 to 0.5 h at a temperature between 35 and 40° C., and stopping the peroxidase reaction by adding an effective quantity of sulfuric acid.

J) A step of analysis, in which the microtiter plate is analyzed using a reading device for ELISA plates, preferably at 492 nm.

In a specific embodiment, the antigen suspension is obtained by suspending liposomes in a buffer solution at a pH between 7.0 to 7.4, at 1 to 5 mmole antigen per liter of buffer solution.

The blocking solution includes a buffer solution at a pH between 7.0 to 7.4, and a solution with a high protein concentration, preferably gelatin at 0.4%, weight by volume, with or without an effective quantity of a lipidic particle-inducer agent, preferably with the effective quantity and the lipidic particle-inducer agent used to form the antigen.

In a preferred embodiment, the effective quantity of the antigen suspension in step A is 50 to 100 ml. The secondary antibody can be also conjugated to the enzyme alkaline phosphatase instead of peroxidase, in this case the corresponding alkaline phosphatase substrate is used.

In a specific embodiment, the hapten solution is obtained dissolving hapten in a buffer solution at a pH between 7.0 and 7.4, at 0.1 to 10 mmoles of hapten per liter of buffer solution.

In relation to the stabilization of membranes with drugs that avoid the formation of lipidic particles in liposomal model membranes or in cellular membranes, which in turn avoid the subsequent binding of anti-lipidic particle antibodies, the studies were carried out with liposomal or cellular antigens using the cytofluorometry method. In a favorite modality, this method includes the following steps:

A) A first step of incubation, in which the antigen suspension, liposomes or cells, are incubated with a drug that stabilizes lipidic bilayers, this drug being used at a concentration of 0.1 up to 100 mM, and the obtained mixture is incubated for 0.25 to 2 h at a temperature between 35 and 40° C.

B) A first step of addition and incubation, in which the antibody porter is added to the antigen stabilized with the stabilizer drug, this antibody porter is diluted from 1:5 up to 1:1000 into a buffer solution at a pH between 7.0 to 7.4, and the resulting mixture is incubated for 0.25 to 2 h at a temperature between 35 and 40° C.

C) A first step of washing, in which the antigen, stabilized with stabilizer drug and bound to the antibody porter, is washed with a buffer solution at a pH between 7.0 to 7.4, with or without an effective quantity of a lipidic particle-inducer agent, preferably with the effective quantity of the inducer agent used to obtain the antigen.

D) A step of recovery, in which the antigen stabilized with stabilizer drug and bound to the antibody porter is recovered, preferably by centrifugation.

E) A second step of addition and incubation, in which an effective quantity of a secondary antibody is added to the antigen stabilized with the stabilizer drug and bound to antibody porter. The resulting mixture is incubated for 0.25 to 2 h in darkness at a temperature between 35 to 40° C. The secondary antibody is selected preferably from antibodies from a different species from that of the antibody porter and can be anti-IgG, IgA or IgM Fc (human or the animal in study), or anti-IgM or IgG Fc antibodies depending on the nature of the monoclonal antibody when this is the antibody porter. The secondary antibody is used at a final dilution between 1:25 to 1:500 in a buffer solution at a pH between 7.0 to 7.4, and is conjugated to a substance or fluorescent substrate, preferably to FITC.

F) A second step of washing, in which the antigen stabilized with the stabilizer drug and bound to the antibody porter and the secondary antibody is washed with a buffer solution at a pH between 7.0 to 7.4, with or without an effective quantity of a lipidic particle-inducer agent, preferably with the same quantity and the same inducer agent used to obtain the antigen.

G) A step of suspension and analysis, in which the antigen stabilized with the stabilizer drug and bound to the antibody porter and the secondary antibody are suspended in a transporting solution, selected preferably from FACS Flow™ (Beckton Dickinson™ Co.) and Haema Line 2™ (Serotono-Baker Diagnostics™, INC) at 1 to 5 mmole of antigen per liter of solution; this solution being preferably filtered previously with a 0.22 μm pore diameter Millerpore™ filter, the obtained mixture being analyzed in a flow cytometer, preferably with a single 488 nm argon laser beam.

In a preferred embodiment, the antigen suspension is obtained suspending the antigen in a buffer solution at a pH between 7.0 to 7.4, at 1 to 5 mmole per liter of buffer solution for liposomal antigen. Furthermore, fluorescent substrate can also be selected from the group consisting of phycoerythrin, Cy3 and Percp.

This antigen is incubated with a drug that stabilizes lipidic bilayers, this drug being used at a concentration of 0.1 up to 100 mM, the resulting mixture is incubated for 0.25 to 2 h at a temperature between 35 and 40° C.

In a specific embodiment the antigen can be a liposome suspension or cells from human or animals.

The various aspects of the present invention, will be more clearly illustrated by the following examples, which are presented for illustrative purposes only and they should not be interpreted as limiting.

EXAMPLES

Liposomal antigens used in the examples were characterized by their $^{31}$P nuclear magnetic resonance spectra. These spectra showed lipids associated in bilayers or in lipidic particles in the liposomes as was previously described by Baeza et al. (op. cit., 1995), Aguilar (op. cit., 1997) and Aguilar et al., (op. cit., 1999).

Example 1

Indirect Detection by the Liposomal-ELISA Method of Lipidic Particles Through the Detection of Anti-Lipidic Particle Antibodies in Sera from Patients with Antiphospholipid Syndrome Costar™ microtiter plates, with 96 flat-bottom wells with a high lipidic antigen binding property (Costar™ Co. Cambrige, USA), were coated by the addition of 100 μl per well liposomes made from egg-yolk phosphatidylcholine:phosphatidate (2:1 mole ratio) in Tris-NaCl buffer (10 mM, 1 mM) pH 7, containing 0.1 μmol of phosphatidate, and treated with 5 mM $CaCl_2$ to induce lipidic particle formation. Microtiter plates were incubated 1 h at room temperature. After microtiter plates were incubated, they were blocked for 1 h at room temperature by addition of 200 μl per well of 0.4% (w/v) gelatin in Tris-NaCl buffer (10 mM, 1 mM) pH 7, containing $CaCl_2$ 5 mM. Then, the blocking solution was discarded by suction and 100 μl of human sera from patients with antiphospholipid syndrome, at 1:50 dilution using blocking solution, were quickly added to each well in duplicate, to avoid the wells becoming dry; all solutions were added subsequently in the same way. As a positive control, the supernatant of a hybridoma containing a monoclonal antibody against lipidic particles, IgM isotype, at 1:100 dilution using blocking solution, were added to four wells. Human sera were heated previously at 56° C. for 30 min to inactivate complement. After microtiter plates were incubated 1 h at room temperature, they were washed 4 times with 500 μl of blocking solution. Then 100 μl of peroxidase-conjugated goat anti-human IgG, IgA and IgM Fc antibodies or anti-mouse IgM Fc antibodies at 1:2000 dilution in blocking solution were added to each well, respectively, as secondary antibody. After 1 h of incubation at room temperature, microtiter plates were washed again 4 times with the blocking solution and 100 μl of freshly prepared peroxidase substrate were added to each well (10 mg o-phenylenediamine, 25 ml Tris-NaCl buffer (10 mM, 1 mM) pH 7, and 20 μl of 30% $H_2O_2$) and allowed to incubate in an oven at 37° C. for 20 min. The enzyme reaction was stopped by addition of 50 μl per well 2.5 M sulfuric acid. Absorbances were read at 492 nm in an ELISA Labsystems™ reader Multiskan MS™ model; duplicate values were averaged for each serum sample tested.

As negative controls, the secondary antibody was added to wells in duplicate in the absence of human sera; in addition, human sera and the secondary antibody were added to wells in duplicate without liposomal antigens.

Results obtained by the liposomal-ELISA method were expressed in Arbitrary Units (AU) which are determined by the following equation:

$$AU = \frac{AsP - AsW}{AsH - AsW}$$

Where:
AsP=Absorbance at 492 nm of patients sera;
AsW=Absorbance at 492 nm of the control without human sera; and
AsH=Absorbance at 492 nm of healthy blood donors sera.

To determine the isotype of anti-lipidic particle antibodies, human sera that gave a positive reaction were analyzed again but peroxidase-conjugated goat anti-human IgG or IgM Fc antibodies were used as a secondary antibody; in order to determine whether the anti-lipidic particle antibodies correspond to the IgG or IgM isotype, respectively.

Analyzed Human Sera.

Sera studied were obtained from the Bank of the Laboratory of Immunology of the Specialities Hospital of La Raza Medical Center México, D. F., México, and they came from thirty patients positive for anti-cardiolipin antibodies of the IgM or IgG isotype. Eleven patients meet with four or more of the American Rheumatism Association criteria for systemic lupus erythematosus (Tan et al., 1982, Arthritis Rheum. 25:1271-1277), twelve meet with the criteria for primary antiphospholipid syndrome (Asherson et al., op. cit., 1996; Piette et al., 1993, J. Rheumatol. 20:1802-1804), and seven for antiphospholipid syndrome secondary to systemic lupus erythematosus (Asherson et al., op. cit., 1996) (Table 1).

Anti-cardiolipin antibodies were detected using cardiolipin coated to ELISA microtiter plates as antigen (Loizou et al., 1985, Clin. Exp. Immunol. 62:738-745). These results are also expressed in Arbitrary Units (AU) and they are considered positive when they have values $\geq 1.9$ AU for IgG isotype, and $\geq 2.4$ AU for IgM isotype (Loizou et al., op. cit., 1985). All patient sera were positive for IgG isotype and some of them were positive for IgM isotype (Table 2).

TABLE 1

Criteria for the classification of primary antiphospholipid syndrome, systemic lupus erythematosus, and antiphospholipid syndrome secondary to systemic lupus erythematosus from the American Rheumatism Association.

| Systemic lupus erythematosus | Primary antiphospholipid syndrome | Antiphospholipid syndrome secondary to systemic lupus erythematosus |
|---|---|---|
| Serositis: Pleuritis Pericarditis | Venous and arterial thrombosis: Renal complications Pulmonary embolism Cerebral ischemia Necrotic skin ulcerations Myocardial infarction with uremia | Malar rash Discoid rash Oral or pharyngeal ulceration Frank arthritis |
| Nephropathy | Nervous system complications: Stroke and transient attack Neurological disorders | Persistent proteinuria greater than 0.5 g/day |
| Neurologic disorders: Seizures Psychosis | Haematological disorders: Thrombocytopenia Haemolytic anaemia | Pleuritis, in the absence of pulmonary embolism. Pericarditis, in the absence of myocardial infarction or uremia |
| Haematological disorders: Thrombocytopenia Haemolytic anaemia | Antiphospholipid antibodies: Anti-cardiolipin Lupus anticoagulant Anti-phosphatidylethanolamine Anti-phosphatidylserine | Antibodies to native DNA Antiphospholipid antibodies Anti-$\beta_2$-glycoprotein I antibodies |
| Immunologic disorders: False positive VDRL Antibodies to dsDNA Antinuclear antibodies | Anti-$\beta_2$-glycoprotein I antibodies | Venous and arterial thrombosis: Renal complications Pulmonary embolism Cerebral ischemia Necrotic skin ulcerations Myocardial infarction with uremia |
| | Recurrent fetal loss | Lymphopenia less that 1000/$\mu$l Recurrent fetal loss |

TABLE 2

Detection of anti-cardiolipin and anti-lipidic particles antibodies in human sera

| Healthy blood donors | Anti-cardiolipin Antibodies (ELISA) | | Anti-lipidic particles Antibodies (liposomal antigen made from phosphatidylcholine: phosphatidate (2:1) + CaCl$_2$) (Cytofluorometry) | Patients' sera and diagnostic | Anti-cardiolipin antibodies (ELISA) | | Anti-lipidic particles antibodies (liposomal antigen made from phosphatidylcholine: phospatidate (2:1) + CaCl$_2$) (Cytofluorometry) | | |
|---|---|---|---|---|---|---|---|---|---|
| | IgM (+) $\geq$ 2.4 AU | IgG (+) $\geq$ 1.9 AU | Positive results at: (+) D $\geq$ 0.5, p < 0.001 (Polyvalent) | | IgM (+) $\geq$ 2.4 AU | IgG (+) $\geq$ 1.9 AU | Positive results at: (+) D $\geq$ 0.5, p < 0.001 | | |
| | | | | | | | Polyvalent | IgM | IgG |
| 1H | — | — | — | AC11 PAPS | — | 7.5 | D = 0.76 | — | D = 0.54 |
| 2H | — | — | — | AC12 PAPS | — | 56.3 | D = 0.77 | — | D = 0.70 |

TABLE 2-continued

Detection of anti-cardiolipin and anti-lipidic particles antibodies in human sera

| Healthy blood donors | Anti-cardiolipin Antibodies (ELISA) | | Anti-lipidic particles Antibodies (liposomal antigen made from phosphatidylcholine: phosphatidate (2:1) + $CaCl_2$) (Cytofluorometry) | Patients' sera and diagnostic | Anti-cardiolipin antibodies (ELISA) | | Anti-lipidic particles antibodies (liposomal antigen made from phosphatidylcholine: phospatidate (2:1) + $CaCl_2$) (Cytofluorometry) | | |
|---|---|---|---|---|---|---|---|---|---|
| | IgM (+) ≧ 2.4 AU | IgG (+) ≧ 1.9 AU | Positive results at: (+) D ≧ 0.5, p < 0.001 (Polyvalent) | | IgM (+) ≧ 2.4 AU | IgG (+) ≧ 1.9 AU | Positive results at: (+) D ≧ 0.5, p < 0.001 Polyvalent | IgM | IgG |
| 3H | — | — | — | AC13 SLE | 5.24 | 17.2 | D = 0.77 | D = 0.65 | D = 0.70 |
| 4H | — | — | — | AC14 SLE | — | 10.6 | D = 0.74 | D = 0.65 | D = 0.62 |
| 5H | — | — | — | AC15 PAPS | — | 6.7 | D = 0.74 | D = 0.50 | D = 0.84 |
| 6H | — | — | — | AC16 SLE | — | 2.52 | D = 0.75 | D = 0.56 | D = 0.59 |
| 7H | — | — | — | AC17 SLE | — | 4.3 | D = 0.75 | — | D = 0.59 |
| 8H | — | — | — | AC18 SLE + APS | — | 67.4 | D = 0.73 | — | D = 0.63 |
| 9H | — | — | — | AC19 SLE | — | 13.6 | D = 0.73 | D = 0.72 | D = 0.73 |
| 10H | — | — | — | AC20 SLE | — | 9.3 | D = 0.75 | D = 0.52 | D = 0.73 |
| 11H | — | — | — | AC21 PAPS | — | 3.36 | D = 0.75 | — | D = 0.62 |
| 12H | — | — | — | AC22 SLE + APS | 2.8 | 15.4 | D '2 0.56 | D = 0.52 | D = 0.61 |
| 13H | — | — | — | AC23 SLE + APS | — | 19.2 | D = 0.59 | — | D = 0.61 |
| 14H | — | — | — | AC24 PAPS | — | 18.0 | D = 0.61 | — | D = 0.61 |
| 15H | — | — | — | AC25 PAPS | 3.95 | 16.3 | D = 0.53 | — | D = 0.62 |
| 16H | — | — | — | AC26 SLE | 3.06 | 9.2 | D '2 0.53 | — | D = 0.62 |
| 17H | — | — | — | AC27 PAPS | — | 8.6 | D = 0.51 | — | D = 0.54 |
| 18H | — | — | — | AC28 PAPS | — | 11.5 | D = 0.51 | — | D = 0.54 |
| 19H | — | — | — | AC29 SLE | — | 11.08 | D = 0.43 | D = 0.52 | D = 0.57 |
| 20H | — | — | — | AC30 PAPS | — | 14.7 | N/D | D = 0.52 | D = 0.57 |
| 21H | — | — | — | AC31 SLE + APS | — | 19.4 | D = 0.66 | D = 0.66 | D = 0.50 |
| 22H | — | — | — | AC32 SLE + APS | 3.0 | 39.6 | D '2 0.56 | — | D = 0.57 |
| 23H | — | — | — | AC33 PAPS | — | 23.7 | D = 0.56 | — | D = 0.54 |
| 24H | — | — | — | AC34 SLE + APS | — | 34.4 | D = 0.56 | — | D = 0.74 |
| 25H | — | — | — | AC35 PAPS | 4.0 | 18.0 | D '2 0.66 | D = 0.56 | D = 0.75 |
| 26H | — | — | — | AC36 SLE | 44.0 | 158.0 | D = 0.64 | D = 0.60 | D = 0.64 |
| 27H | — | — | — | AC37 SLE | — | 11.0 | D '2 0.64 | D = 0.70 | D = 0.75 |
| 28H | — | — | — | AC38 PAPS | 3.0 | 2.0 | D = 0.64 | D = 0.59 | D = 0.75 |
| 29H | — | — | — | AC39 SLE + APS | — | 52.0 | D = 0.64 | D = 0.76 | D = 0.75 |
| 30H | — | — | — | AC40 SLE | 4.0 | 18.0 | D = 0.66 | D = 0.56 | D = 0.75 |

PAPS-Primary antiphospholipid syndrome.
SLE-Systemic lupus erythematosus.
APS + SLE-Antiphospholipid syndrome secondary to systemic lupus erythematosus Sera from healthy blood donors, in other words, of healthy subjects which were used as negative controls in the analyzed immunoreactions, did not show anti-cardiolipin antibodies of IgM or IgG isotype (Table 2). These sera came from the Bank of Blood of La Raza Medical Center, México, D. F., México.

Patients' sera and sera from healthy blood donors were supplied us by Dr. Carlos Lavalle Montalvo, Manager of the Infectology Hospital of La Raza Medical Center, México, D. F., México.

Results of the Detection by the Liposomal-ELISA Method of Anti-Lipidic Particle Antibodies in Human Sera.

Reaction of human sera from healthy blood donors or from patients with antiphospholipid syndrome with liposomal antigens made from egg-yolk phosphatidylcholine:phosphatidate (2:1 mole ratio) in Tris-NaCl buffer (10 mM, 1 mM) pH 7, containing 0.1 mmol of phosphatidate, and treated with 5 mM $CaCl_2$ to induce lipidic particles formation, is shown in FIG. 1. Immunoreaction of patient sera with the lipidic particles was clearly different from that of healthy blood donors sera or control sera, since the reaction with the peroxidase substrate was negative when control sera were used. In general, control serum gave values smaller than one AU. All the values from control sera were combined to obtain the arithmetic mean and the standard deviation. We then consider as positive all results greater than 3 standard deviations from the mean. After this analysis, sera from the 30 healthy blood donors were mixed and the mixture was used as a control serum for subsequent analysis. In FIG. 1, the dark line indicates the upper limit above which the reactions of sera with lipidic antigens are positive. The reaction of most of the patient sera was clearly positive, with values of AU higher than 6.

Arbitrary unit data for 7 sera (AC12, AC14, AC15, AC16, AC31, AC32 and AC34) are shown in FIG. 1. These sera are representative of the 30 analyzed sera. AC12 and AC15 sera correspond to patients with primary antiphospholipid syndrome (PAPS); AC14 and AC16 sera are from patients with systemic lupus erythematosus (SLE) and AC31, AC32, and AC34 sera are from patients with antiphospholipid syndrome secondary to systemic lupus erythematosus (APS+SLE). In this Figure, the reaction of H308 monoclonal antibody with liposomal antigens from egg-yolk phosphatidylcholine:phosphatidate (2:1 mole ratio) in Tris-NaCl buffer (10 mM, 1 mM) pH 7, containing 0.1 mmol of phosphatidate, and treated with 5 mM $CaCl_2$ to induce lipidic particles formation is shown as a positive control. Peroxidase-conjugated goat anti-human IgG Fc antibodies were used as secondary antibody for the human sera and anti-mouse IgM Fc for the monoclonal antibody, both at 1:2000 final dilution.

An important particularity of liposomal-ELISA method is that it allows the simultaneous determination of anti-lipidic particle antibodies in at least 40 sera samples by microtiter plate, each one in duplicate; for this reason this method can be easily applied to the diagnosis of illnesses where this type of antibody is presented.

Example 1A

Comparative Study when Antigens without Lipidic Particles and Sera from Patients with the Antiphospholipid Syndrome are Used in the Liposomal-ELISA Method Example 1 was repeated but using as antigens "rigid" liposomes made from dipalmitoylphosphatidylcholine:egg-yolk phosphatidylcholine:dipalmitoylphosphatidate (1.2:0.8:1.0 mole ratio) in Tris-NaCl buffer (10 mM, 1 mM) pH 7, which when incubated with 5 mM $BaCl_2$ retain a smooth bilayer surface. In this case, the reaction of peroxidase substrate conjugated to the secondary antibody was negative. Because these liposomes did not have any lipidic particles, the anti-lipidic particle antibodies did not react with them and consequently the secondary antibody did not bind these liposomes, which explains the negative reaction of peroxidase substrates. These results disprove the possibility that anti-lipidic particle antibodies recognize a lipid-divalent cation complex and/or the reduction in the liposomal surface charge due to the binding of divalent cations without changes in bilayer lipid arrangements to lipidic particle arrangements (Aguilar et al., op. cit., 1999).

Example 1B

Comparative Study when Antibodies Different to the Anti-Lipidic Particle Antibodies and Liposomal Antigens Bearing Lipidic Particles are Used in the Liposomal-ELISA Method Example 1 was repeated with some modifications. In this experiment, liposomes made from egg yolk phosphatidylcholine:phosphatidate (2:1 mole ratio) in Tris-NaCl buffer (10 mM, 1 mM) pH 7, containing 0.1 µmol of phosphatidate and treated with 5 mM $CaCl_2$ to induce lipidic particles formation, were incubated directly with peroxidase-conjugated goat anti-anti-human IgG, IgA and IgM Fc antibodies, or with the supernatant of a hybridoma producing unrelated IgM isotype monoclonal antibodies, such as those against a membrane protein of *Trichinella spiralis* and peroxidase-conjugated goat anti-mouse IgM Fc antibodies. In both cases, the reaction with peroxidase substrate was negative, because in absence of human anti-lipidic particle antibodies or mouse anti-lipidic particle monoclonal antibody, the secondary antibody, (peroxidase-conjugated goat anti-human IgG, IgA and IgM Fc or anti-mouse IgM Fc antibodies) do not bind directly to lipidic particles induced by calcium in liposomal antigens.

Example 1C

Comparative Study when Anti-Lipidic Particle Antibodies and Secondary Antibody are Used in the Absence of Liposomal Antigens Bearing Lipidic Particles in the Liposomal-ELISA Method Example 1 was repeated but in the absence of liposomal antigens. In consequence, the reaction of peroxidase substrate conjugated to secondary antibody was negative. Because anti-lipidic particle antibodies do not bind directly to the microtiter plate (which could give a false positive result) because microtiter plate was blocked with the gelatin that is used in this methodology, the secondary antibody does not bind to microtiter plate, which explains the negative reaction of the peroxidase substrate conjugated to the secondary antibody.

From these examples we can conclude that, in a preferred embodiment of the present invention, a diagnostic kit particularly useful for detection using liposomal-ELISA of anti-lipidic particle antibodies in at least a serum sample from a subject suffering from an illness related to antiphospholipid antibodies includes an indicator reagent including, firstly, at least liposomes with lipidic particles and, secondly, at least an anti-lipidic particle monoclonal antibody; at least a blocking solution to prevent possible false positive results from occurring; at least a buffer solution (as a medium to allow the reaction between the sample coming from the sick person to proceed with this indicator reagent) enzymatic media that preferably include the peroxidase enzyme (to detect this reaction); and at least a sample of a reference serum coming from a healthy individual (as a negative control for the reaction with liposomal antigens bearing lipidic particles).

In this preferred embodiment of the diagnostic kit, the serum sample coming from the ill subject is made to react with the indicator reagent containing liposomes bearing lipidic particles. Also, the indicator reagent containing liposomes with lipidic particles is made to react with the anti-lipidic particle monoclonal antibody, as a positive control (to show that the system to detect the reaction between anti-lipidic particle antibodies from the serum of a subject suffering from an illness associated with antiphospholipid antibodies and the antigen bearing lipidic particles works correctly).

In an alternative embodiment, the diagnostic kit also comprises one or more microtiter plate(s) to contain the reaction. In the same fashion, in another alternative modality, the sample of serum from a healthy individual is not included in the kit, and in this case is obtained from an external source. This serum sample comes from a healthy individual who does not present an illness associated with antiphospholipid antibodies.

Example 2

Cytofluorometric Detection of the Liposomal Antigen Autofluorescence

One hundred microliter samples of liposomes made from egg yolk phosphatidylcholine:phosphatidate, (2:1 mole ratio) in Tris-NaCl buffer (10 mM, 1 mM) pH 7, containing 0.1 µmol of phosphatidate were analyzed in a FACSCalibur™ Flow Cytometer equipped with a single 488 nm argon laser beam (Beckton Dickinson™). Autofluorescence readings were obtained from 10,000 liposomes in a logarithmic mode and they were made in the FL-1 channel at 748 V (Baeza et al., op. cit. 1995). The obtained data were analyzed with the Cellquest™ program (Beckton Dickinson™).

Figure 2:
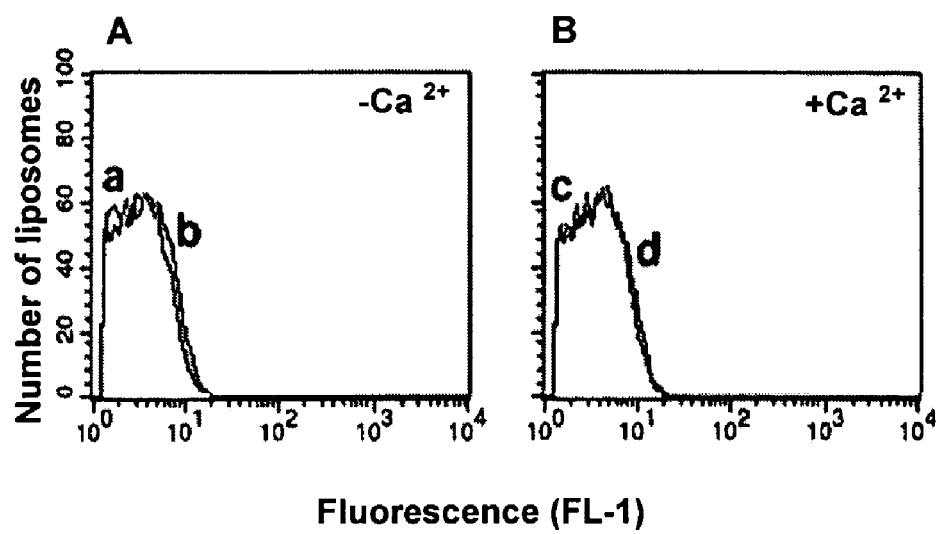
FIGS. 2A and 2B illustrate the fluorescence graphs of liposomes made from PC:PA (2:1 mole ratio), with and without lipidic particles induced by calcium, that were incubated with Tris-NaCl (10 mM, 1 mM) pH 7, or with a secondary antibody conjugated to peroxidase.

Autofluorescence histograms obtained from egg yolk phosphatidylcholine:phosphatidate (2:1 mole ratio) liposomes showed values between 1 to 10 fluorescence units (a, FIG. 2A). The detection of liposomal autofluorescence allowed the application of cytofluorometry to the analysis of immunologic reactions where liposomal antigens are used. Liposomal autofluorescence (a, FIG. 2A) was not modified when liposomes were incubated with 5 mM $CaCl_2$ (c, FIG. 2B), which indicates that the presence of lipidic particles in liposomes did not modify the liposomal autofluorescence.

Furthermore, this fluorescence was not modified by the addition of FITC-conjugated goat anti-human IgG, IgA and IgM Fc or anti-mouse IgM Fc antibodies as secondary antibodies, which indicates that these antibodies do not bind directly to liposomal antigens, and therefore they can not produce a false positive reaction. Results with the FITC-conjugated goat anti-human IgG, IgA and IgM Fc antibodies as secondary antibody at 1:200 final dilution are shown in b, FIG. 2A and d, FIG. 2B (with liposomal antigens in the absence of calcium (b, FIG. 2A) and in presence of this divalent cation (d, FIG. 2B)).

Similar results were obtained with liposomes made from phosphatidylcholine; phosphatidylcholine:cardiolipin (2:1 mole ratio); phosphatidylcholine:phosphatidylserine (4:1 mole ratio) or dipalmitoylphosphatidylcholine:egg-yolk phosphatidylcholine:dipalmitoylphosphatidate (1.2:0.8:1 mole ratio), respectively. Therefore cytofluorometry can be applied generally to the analysis of immunologic reactions where liposomal antigens with different lipidic formulations are used.

Example 2A

Detection by the Liposomal Cytofluorometry Method of Lipidic Particles in Liposomes Using H308 Monoclonal Antibody One hundred microliter samples of liposomes made from egg yolk phosphatidylcholine:phosphatidate (2:1 mole ratio) in Tris-NaCl buffer (10 mM, 1 mM) pH 7, containing 0.1 μmol of phosphatidate, and treated with 5 mM $CaCl_2$ to induce lipidic particle formation, were placed in 14×95 mm ultracentrifuge tubes (Beckman ultra-clear No. 344060). To each one of these aliquots the supernatant of a 1:100 final dilution in Tris-NaCl buffer (10 mM, 1 mM), pH7, of the H308 hybridoma (which generates an anti-lipidic particle monoclonal antibody) was added. After incubation for 1 h at 37° C., the liposomes were washed with 12 ml of Tris-NaCl buffer (10 mM, 1 mM) pH 7, containing 5 mM $CaCl_2$. Liposomes were recovered by centrifugation in ultracentrifuge (Beckman L8-M™) at 202,000×g for 50 min at 18° C. Next, FITC-conjugated goat anti-mouse IgM Fc antibodies, at 1:200 final dilution into Tris-NaCl buffer (10 mM, 1 mM) pH 7, was added to each tube as secondary antibody and incubated for 1 h at 37° C. in the darkness. At the end of the incubation, the liposomes were washed as previously indicated. Finally, the liposome preparation was resuspended in 500 μl of FACS flow solution (Beckton Dickinson™ Co.) filtered with a 0.22 μm pore diameter Millipore™ filter. This liposomal suspension was analyzed by cytofluorometry in a FACSCalibur™ Flow Cytometer equipped with a single 488 nm argon laser beam (Beckton Dickinson™).

Fluorescence readings were made using the FL-1 channel. Relative size and/or liposomal aggregation was analyzed by diffraction of the laser beam in the FSC (forward scatter light) channel and the granularity or liposomal bilayers complexity was analyzed by refraction and reflection of the laser in the SSC (side scatter light) channel. Analysis of 10,000 liposomes was performed in a logarithmic scale with the following detectors: FSC in E00, with a detector compensation threshold of 52 V; SSC of 401 V and FL-1 of 748 V (Baeza et al., op. cit., 1995). The obtained data were analyzed with the Cellquest™ program (Beckton Dickinson™).

"Rigid" liposomes made from dipalmitoylphosphatidylcholine:egg-yolk phosphatidylcholine:dipalmitoylphosphatidate (1.2:0.8:1.0 mole ratio) in Tris-NaCl buffer (10 mM, 1 mM) pH 7, alone or incubated with $BaCl_2$ 5 mM were also used as antigens.

The H308 monoclonal antibody does not react with bilayer lipid arrangements, since the fluorescence detected from smooth liposomes incubated with this monoclonal antibody (a, FIG. 3A) was similar to the autofluorescence of control liposomes, in Tris-NaCl or treated with calcium, that were not incubated with monoclonal antibody (g, h, FIG. 3D). Furthermore, SSC and FSC values indicated the absence of lipidic particles or liposomal aggregation in smooth liposomes that were not treated with calcium (i, FIG. 3E; k, FIG. 3F) no matter if they were incubated with H308 monoclonal antibody (c, FIG. 3B; e, FIG. 3C). On the contrary, the 60-fold increase in the fluorescence of liposomes treated with calcium (b, FIG. 3A) compared to the fluorescence of liposomes with lipids in bilayers (a, FIG. 3A) (with a value in the fluorescence difference among these liposomal populations in a logarithmic scale (D)=0.9 at p<0.001) showed the reaction of H308 monoclonal antibody with lipidic particles induced by calcium. A value of D≦0.5 at p<0.001 indicates a difference among the studied populations that is highly significant from a statistical point of view (Lampariello, 2000, Cytometry 39:179-188). Therefore, values of D≦0.5 at p<0.001 were considered positive results indicating the presence of anti-lipidic particle antibodies in the analyzed samples.

On the other hand, SSC values indicated that the pattern of lipidic particles was different after the immunoreaction (d, FIG. 3B) compared with the pattern of these lipidic structures in liposomes that were not incubated with H308 monoclonal antibody (j, FIG. 3E); these profiles reflect the dynamic properties of lipidic particles. Besides, liposomal aggregation, was discarded, because FSC values that show liposomal aggregation were similar after the immunoreaction (f, FIG. 3C) to those of liposomes with lipidic particles that were not incubated with H308 monoclonal antibody (l, FIG. 3F).

Monoclonal antibody reaction with lipidic particle liposomal antigens is considered to be a positive indicating that the reaction of patient antibodies with this type of lipidic structure. In consequence, it is necessary to include this determination as a positive control when detecting anti-lipidic particle antibodies in sera from human individuals or animals by liposomal cytofluorometry.

On the other hand, an IgM isotype monoclonal antibody unrelated to the liposomal system analyzed, such as one directed against a membrane protein of *Trichinella spiralis*, did not demonstrate the same reactions for H308 monoclonal antibody with lipidic particles (since cytofluorometry graphs obtained with this unrelated monoclonal antibody were similar to those of control liposomes treated with calcium in absence of H308 monoclonal antibody (h, FIG. 3D; j, FIG. 3E; and l, FIG. 3F)).

"Rigid" liposomes made from dipalmitoylphosphatidylcholine:egg-yolk phosphatidylcholine:dipalmitoylphosphatidate (1.2:0.8:1.0 mole ratio) in Tris-NaCl buffer (10 mM, 1 mM) pH 7, that were incubated with 5 mM $BaCl_2$ retained the smooth bilayer surface and did not show any reaction with H308 monoclonal antibody, because the cytofluorometry graphs obtained (m, FIG. 3G; p, FIG. 3H; and r, FIG. 3I) were similar to those of liposomes that were not treated with $BaCl_2$ or with the monoclonal antibody (m, FIG. 3G; o, FIG. 3H; and q, FIG. 3I).

Example 2B

Indirect Detection by the Liposomal Cytofluorometry Method of Lipidic Particle Through the Detection of Anti-Lipidic Particles Antibodies in Sera from Patients with Antiphospholipid Syndrome This detection is similar to the one described in Example 2A, however sera from patients with antiphospholipid syndrome were used as the antibody carrier instead of H308 monoclonal antibody. One hundred microliter samples of liposomes made from egg yolk phosphatidylcholine:phosphatidate (2:1 mole ratio) in Tris-NaCl buffer (10 mM, 1 mM) pH 7, containing 0.1 mmol of phosphatidate and treated with 5 mM $CaCl_2$ to induce lipidic particles formation, were placed in 14×95 mm ultracentrifuge tubes (Beckman UltraClear™ No. 344060). Sera from patients with antiphospholipid syndrome at 1:50 final dilution into Tris-NaCl buffer (10 mM, 1 mM) pH 7, were added to each ultracentrifuge tube and they were incubated for 1 h at 37° C. Sera were previously heated at 56° C. for 30 min to inactivate complement. After incubation, liposomes were washed with 12 ml of Tris-NaCl buffer (10 mM, 1 mM) pH 7, containing 5 mM $CaCl_2$. Liposomes were recovered by centrifugation in the ultracentrifuge Beckman™ L8-M at 202,000×g for 50 min at 18° C. Next FITC-conjugated goat anti-human IgG, IgA and IgM Fc antibodies were added to each tube at 1:200 final dilution in Tris-NaCl buffer (10 mM, 1 mM) pH 7 as secondary antibody and incubated 1 h at 37° C. in the darkness. At the end of incubation, liposomes were washed as previously indicated. Finally, liposome preparations were resuspended in 500 µl of FACS flow solution (Beckton Dickinson™ Co.) filtered with a 0.22 µm pore diameter Millipore™ filter. This liposomal suspension was analyzed by cytofluorometry in a FACSCalibur™ Flow Cytometer equipped with a single 488 nm argon laser beam (Beckton Dickinson™).

Fluorescence readings were made using the FL-1 channel. Relative size and/or liposomal aggregation was analyzed in the FSC channel and granularity or liposomal bilayers complexity was analyzed in the SSC channel. Analysis of 10,000 liposomes was performed in a logarithmic mode with the following detectors: FSC in E00, with a detector compensation threshold of 52 V; SSC of 401 V and FL-1 of 748 V (Baeza et al., op. cit., 1995). The obtained data were analyzed with the Cellquest™ program (Beckton Dickinson™).

As a negative control, the reaction of healthy blood donor serum with liposomes made from egg yolk phosphatidylcholine:phosphatidate (2:1 mole ratio) in Tris-NaCl buffer (10 mM, 1 mM) pH 7, containing 0.1 mmol of phosphatidate, and treated with 5 mM $CaCl_2$ to induce lipidic particle formation was analyzed. FITC-conjugated goat anti-human IgG, IgA and IgM Fc antibodies were used as secondary antibody.

Thirty healthy blood donor sera were studied. These sera did not present any immunoreaction with lipidic particles, since fluorescence graphs obtained with liposomes incubated with them were similar to those of control liposomes that were incubated with 5 mM $CaCl_2$ only (h, FIG. 3D; and j, FIG. 3E from Example 2A). After this analysis, sera from the 30 healthy blood donors were mixed and the mixture was used as a control serum for subsequent analysis. Cytofluorometry graphs of mixed sera are presented in: a, FIGS. 4A, D, G, J, M, P, S and V; in c, FIGS. 4B, E, H, K, N, Q, T and W, and in e, FIGS. 4C, F, I, L, O, R, U and X. FSC values (e, FIGS. 4C, F, I, L, O, R, U and X) showed the absence of liposomal aggregation by treatment with healthy blood donor serum, because they were very similar to those of liposomes control in absence of human serum indicated in: l, FIG. 3F, from Example 2A.

Immunoreaction of all patient sera with liposomal antigens treated with calcium showed a fluorescence 20- to 40-fold higher than that of control sera, with a difference between liposomal fluorescence in a logarithmic scale (D)$\geq$0.5 at p<0.001 (Table 2). Values of D$\geq$0.5 at p<0.001 were considered positive results and to indicate the presence of anti-lipidic particle antibodies in the sera analyzed, in a similar way as it was described for H308 monoclonal antibodies. As an example, fluorescence histograms of eight sera from patients with systemic lupus erythematosus (SLE) (AC19 and AC20), with primary antiphospholipid syndrome (PAPS) (AC15, AC21 and AC30) or with antiphospholipid syndrome secondary to systemic lupus erythematosus (SLE+APS) (AC18, AC22 and AC31) are shown in: b, FIG. 4A; g, FIG. 4D; j, FIG. 4G; m, FIG. 4J; o, FIG. 4M; r, FIG. 4P; u, FIG. 4S; and x, FIG. 4V. In the eight sera, the reaction between anti-lipidic particle antibodies contained in patients' sera and lipidic particles of liposomal antigens, although positive, were clearly different from each other and compared to the reaction of H308 monoclonal antibody (compare d, FIG. 4B; h, FIG. 4E; k, FIG. 4H; n, FIG. 4K; p, FIG. 4N; s, FIG. 4Q; v, FIG. 4T; and y, FIG. 4W with d, FIG. 3B, from Example 2A), which can be attributed to the polyclonal origin of human antibodies.

SSC values (d, FIG. 4B; h, FIG. 4E; k, FIG. 4H; n, FIG. 4K; p, FIG. 4N; s, FIG. 4Q; v, FIG. 4T; and y, FIG. 4W), a parameter related to liposomal bilayer complexity and therefore the presence of lipids associated in lipidic particles as analyzed, were similar to those of control liposomes incubated with calcium to induce lipidic particles formation (j, FIG. 3E, from Example 2A). Therefore, SSC values showed the presence of lipidic particles in liposomes, which gave the reaction with the anti-lipidic particle antibodies contained in patient sera.

Figure 3:
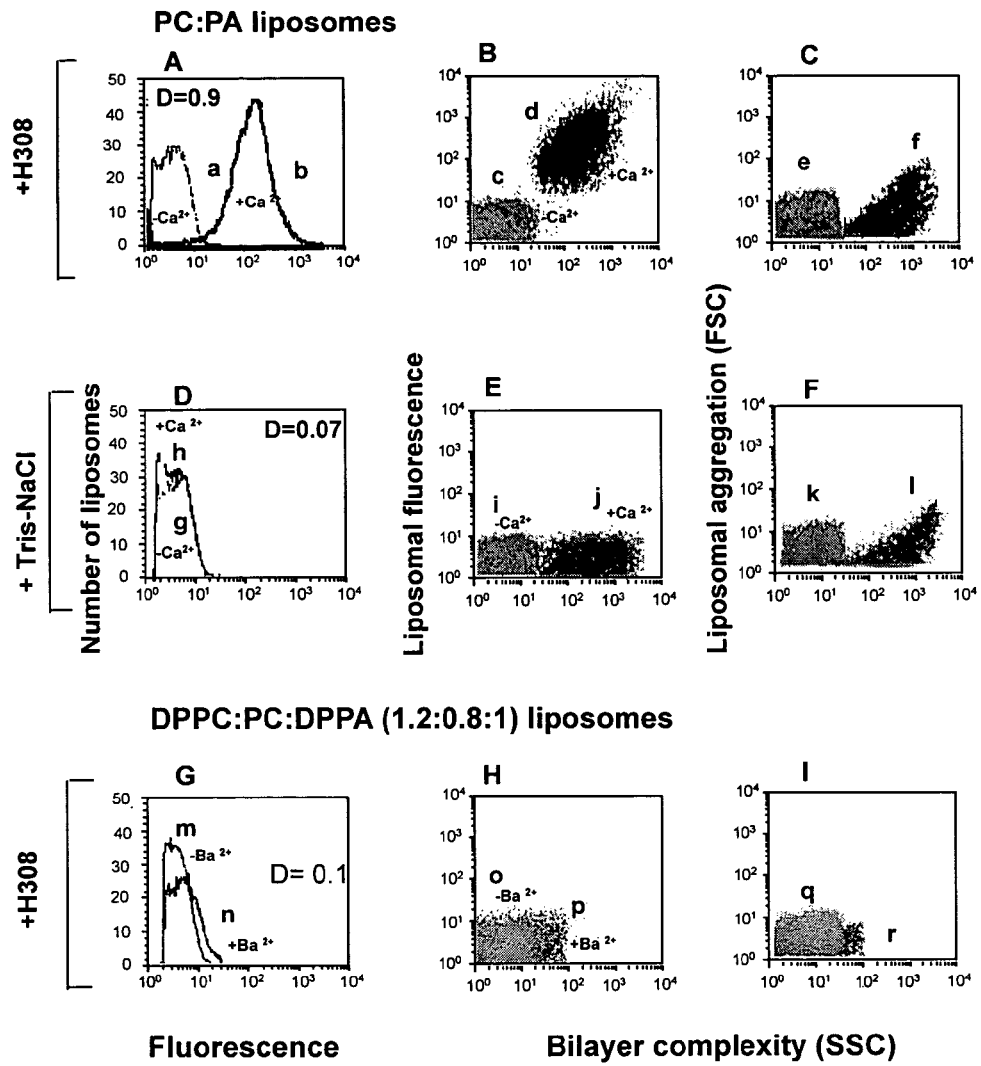
FIGS. 3A-3I show cytofluorometric analysis of the reaction between H308 monoclonal antibody and liposomal antigens made from PC:PA (2:1 mole ratio) or from dipalmitoylphosphatidylcholine:egg-yolk phosphatidylcholine:dipalmitoylphosphatidate (DPPC:PC:DPPA) (1.2:0.8:1 mole ratio) as well as cytofluorometric analysis of liposomal antigens from PC:PA (2:1 mole ratio) in Tris-NaCl (10 mM, 1 mM), with or without lipidic particles induced by calcium, in absence of the H308 monoclonal antibody.
Figure 4:
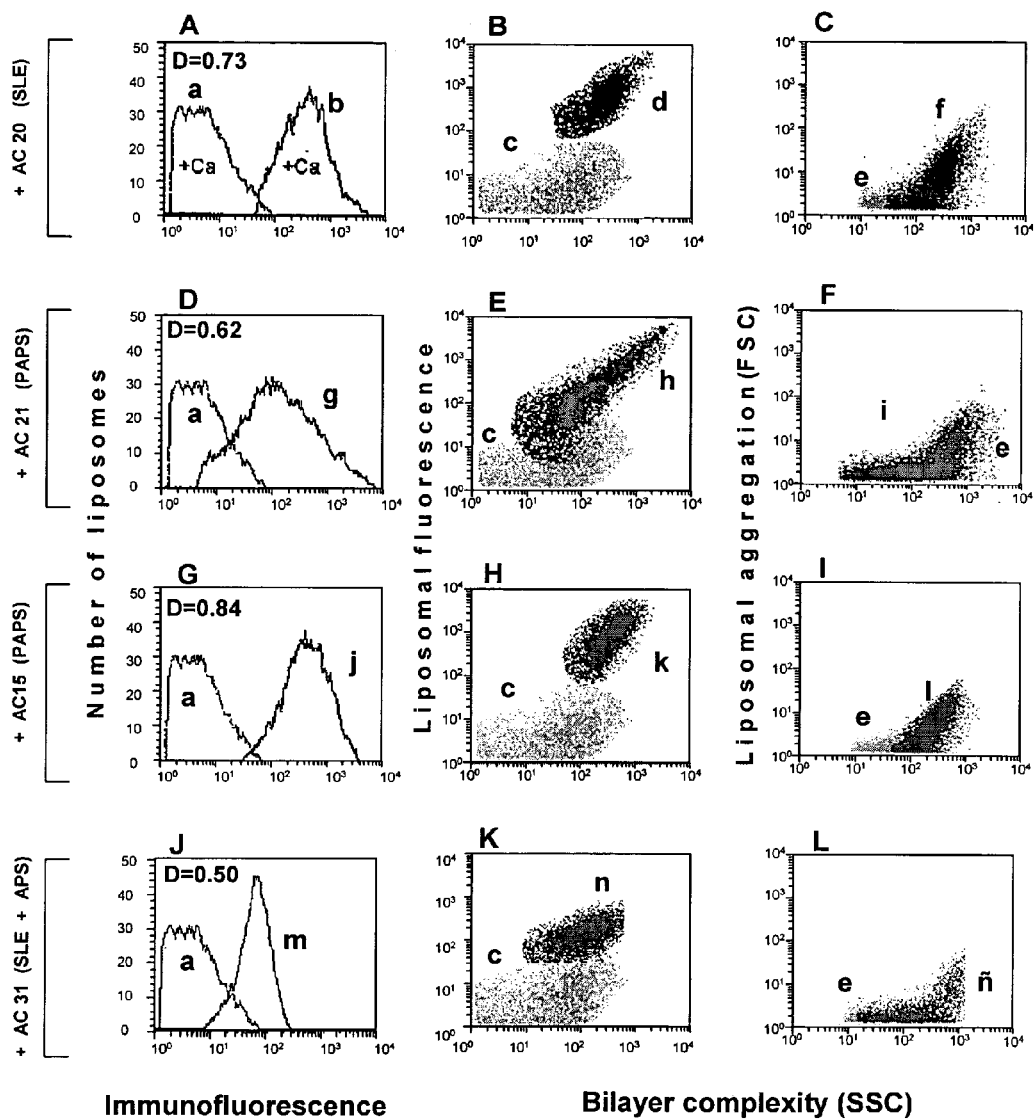
FIGS. 4A-4X show cytofluorometric analysis of the reaction between sera from human healthy blood donors or from patients with antiphospholipid syndrome, and liposomal antigens made from PC:PA (2:1 mole ratio) bearing lipidic particles induced by calcium.
Figure 4:
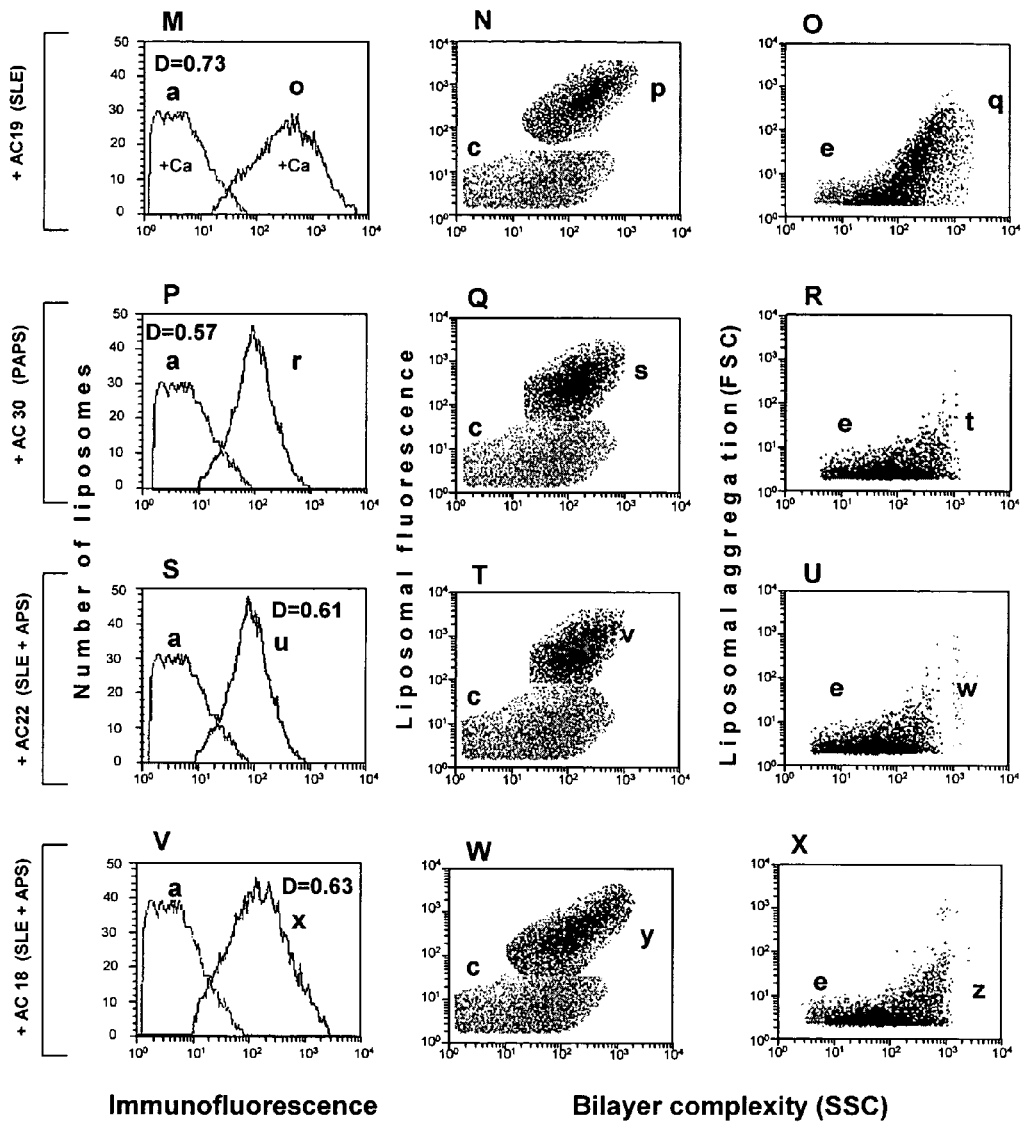

Furthermore, the reaction of patient sera with lipidic particles did not show any liposomal aggregation that could nonspecifically increase the fluorescence registered and give a positive false result, since FSC values (f, FIG. 4C; i, FIG. 4F; l, FIG. 4I; ñ, FIG. 4L; q, FIG. 4O; t, FIG. 4R; w, FIG. 4U; and z, FIG. 4X) were similar, after immunoreaction, to those of liposomes incubated with healthy blood donor serum (e, FIGS. 4C, F, I, L, O, R, U and X) and with those incubated with calcium in the absence of antibodies (l, FIG. 3 F, from Example 2A).

Since the liposomal cytofluorometry method has a sensitivity 10-fold higher than the liposomal-ELISA method in the detection of anti-lipidic particle antibodies it must be applied when a doubtful result has been obtained with liposomal-ELISA method. For example, sera such as AC27 that by the liposomal-ELISA method have a value of AU<1.0, which is negative for the detection of anti-lipidic particle antibodies, show by liposomal cytofluorometry a result of D=0.51, at p<0.001, which is clearly positive for the presence of anti-lipidic particle antibodies.

Example 2C

Comparative Study when Liposomal Antigens without Lipidic Particles and Sera from Patients with Antiphospholipid Syndrome are Used in the Cytofluorometry Method "Rigid" liposomes made from dipalmitoylphosphatidylcholine:egg-yolk phosphatidylcholine:dipalmitoyl-phosphatidate (1.2:0.8:1.0 mole ratio) in Tris-NaCl buffer (10 mM, 1 mM) pH 7 that were incubated with $BaCl_2$, 5 mM, retained a smooth surface and were used as antigens. In "rigid" liposomes, lipidic particles did not form because their rigid bilayers do not allow the lipidic movement that is required to form lipidic particles. These liposomes were incubated with sera from patients with antiphospholipid syndrome and FITC-conjugated goat anti-human IgG, IgA and IgM Fc antibodies and were used at a final dilution of 1:200 as secondary antibody.

Figure 5:
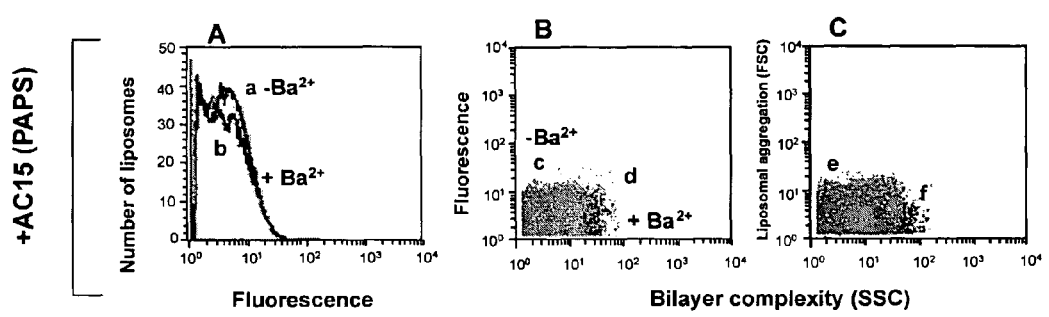
FIGS. 5A-5C show cytofluorometric analysis which indicates that the AC15 serum from a patient with primary antiphospholipid syndrome does not show any immunoreaction with liposomal antigen made from DPPC:PC:DPPA (1.2:0.8:1 mole ratio) that lack lipidic particles.

Cytofluorometry graphs obtained showed that patient sera did not react with "rigid" liposomes treated with $BaCl_2$ (b, FIG. 5A; d, FIG. 5B; and f, FIG. 5C) because they were similar to those of liposomes that were not treated with $BaCl_2$ (a, FIG. 5A; c, FIG. 5B; and e, FIG. 5C). Graphs shown in FIGS. 5A-5C, correspond to the reaction of AC15 serum from a patient with primary antiphospholipid syndrome (PAPS) and are representative of the reaction of sera from the remaining patients indicated in Table 2.

From the above mentioned examples, we can conclude that in another favorite modality of the present invention, a particularly useful diagnostic kit for detection of anti-lipidic particle antibodies in serum from subjects with illnesses associated with antiphospholipid antibodies by liposomal cytofluorometry comprises: an indicator reagent including at least liposomes bearing lipidic particles; at least a buffer solution as a medium to allow the reaction between the ill subject sample and this indicator reagent to proceed; and fluorescent media to make this reaction detectable.

In this preferred embodiment of the diagnostic kit, sera samples from ill subjects are made to react with the indicator reagent containing liposomes bearing lipidic particles.

In an alternative embodiment, the diagnostic kit includes one or more tube(s) for centrifugation to contain and for the development of the reaction.

In the same fashion, in another alternative embodiment, this diagnostic kit can include at least an anti-lipidic particle monoclonal antibody as a positive control for the antibodies reaction with liposomal antigens bearing lipidic particles, and at least a sample of a reference serum from a healthy individual as a negative control for the reaction with liposomal antigens bearing lipidic particles.

In another alternative embodiment, the serum sample of a healthy individual can be obtained from an external source. This serum sample comes from a healthy individual that does not present an illness associated with antiphospholipid antibodies.

Example 3

Direct Detection by the Immunofluorescence Method of Lipidic Particles in Cells from a Subject Using H308 Monoclonal Antibody C5337 cancer pancreas cells were used as antigens. In a 24-well cell culture plate, containing sterile micro cover glasses in each well, $1 \times 10^6$ cells were added by micro cover glass and the plate was incubated at 37° C. in an atmosphere containing 5% $CO_2$. When 90% cellular confluence was reached, cells were washed twice with 2 ml of incomplete DMEM cell culture medium and once with 2 ml of sterile phosphate buffer at pH 7.4. All solutions were quickly added to avoid the cells surface becoming dry. Next, 200 µl of H308 hybridoma supernatant, containing anti-lipidic particle H308 monoclonal antibody, at 1:10 dilution in incomplete DMEM cell culture medium was added, and cells were incubated for 1 h at 37° C. in the presence of 5% $CO_2$. After incubation, cell cultures were washed 3 times with 2 ml of phosphate buffer, pH 7.4 and 200 µl of FITC-conjugated goat anti-mouse IgM Fc antibodies at 1:200 dilution, in incomplete DMEM cell culture medium were added. After incubation for 1 h at 37° C. in the presence of 5% $CO_2$, cell cultures were washed again 3 times with 2 ml of phosphate buffer. Finally, micro cover glasses were mounted on slides with VectaShield™, and the preparations were sealed, observed, and photographed with epifluorescence and Nomarski optics using a Nikon™ Optiphot-2™ microscope.

Figure 6:
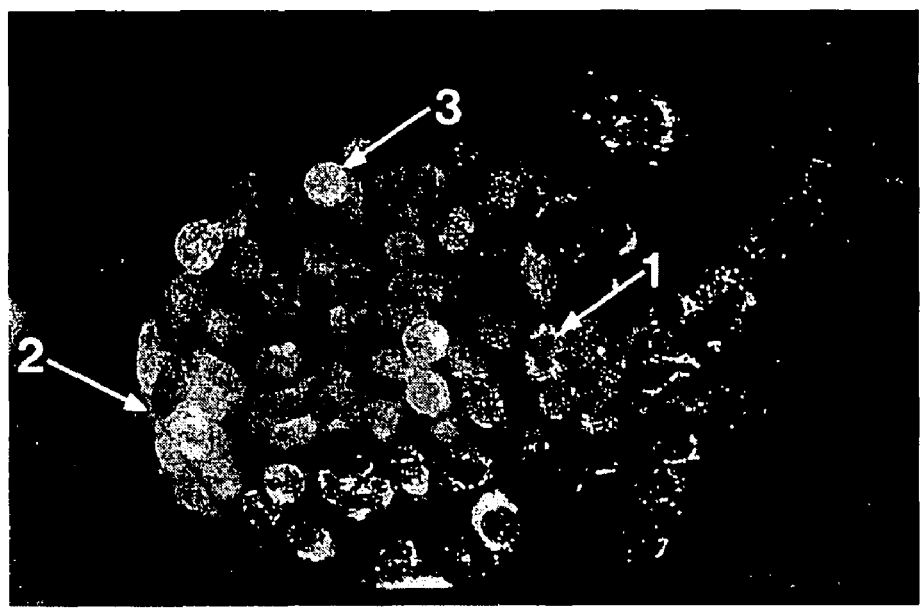
FIG. 6 is a picture of C5337 human pancreas cancer cells that shows the immunoreaction between H308 monoclonal antibody and lipidic particles from the membranes of these cells.

C5337 cancer pancreas cells showed areas with a strong fluorescence intensity located in small points, in occasions above cellular nucleus (1, FIG. 6); in some cases fluorescence was located in cell junctions (2, FIG. 6). In other cases, neoplastic cells were labeled over the whole surface, these cells showing a round morphology (3, FIG. 6) like that corresponding to cells that do not adhere to cell culture plates which can be in apoptosis (programmed cellular death); furthermore, these cells also can not be adhered because they will be in a cellular division process. Immunostaining shows the reaction of monoclonal antibody with lipidic particles present in membranes of C5377 cancer pancreas cells. H308 monoclonal antibody was adsorbed with egg-yolk phosphatidylcholine:phosphatidate liposomes (2:1 molar ratio) in Tris-NaCl buffer (10 mM, 1 mM) pH 7, containing 0.1 µmol of phosphatidate and treated with $CaCl_2$ 5 mM to induce lipidic particle formation, to confirm that the observed immunostaining really showed cellular lipidic particles. After this adsorption, the H308 hybridoma supernatant no longer reacted with C5337 cells because the anti-lipidic particle antibodies from this supernatant were eliminated.

As a negative control, neoplastic cells were incubated with FITC-conjugated secondary antibody or with an unrelated IgM isotype monoclonal antibody directed against a membrane protein of *Trichinella spiralis*. In both cases there was not any reaction of antibodies with neoplastic cells since fluorescence that showed the immunoreaction was not observed.

These studies show that H308 monoclonal antibody, besides reacting with lipidic particles of liposomal membranes, also reacts with membrane lipidic particles from cells in cultures. These cells represent a natural antigen, contrary to liposomes, which are an experimental model of cellular membranes. When human placenta tissue sections (6 mm-thickness) were used, the H308 monoclonal antibody reacted. The immunoreaction varied during the 9 months of the life of this organ and a higher quantity of lipidic particles was detected in the final stages of pregnancy. This reaction showed that H308 monoclonal antibody also reacts with lipidic particles present in nature in this human organ.

In accordance with the above-mentioned studies, detection of lipidic particles in cell membranes can be used to characterize distinct functional states that cells go through during the different stages of cellular cycle, including the apoptosis process (programmed cellular death).

Example 3A

Direct Cytofluorometric Detection of Lipidic Particles in Cells from a Subject Using H308 Monoclonal Antibody A sample of 100,000 platelets in 100 ml of Tris-NaCl buffer (10 mM, 135 mM) pH 7, containing glucose 11 mM, was placed in polystyrene 8×75 mm tubes. To each of these aliquots, H308 hybridoma supernatant at a 1:100 dilution in Tris-NaCl buffer (10 mM, 135 mM) pH 7, containing glucose 11 mM, was added. This hybridoma generates an anti-lipidic particle IgM isotype monoclonal antibody. Additionally, 5 µM adenosine diphosphate (ADP) was added to each tube and they were incubated for 30 min at 37° C. After incubation, platelets were washed with 4 ml of Tris-NaCl buffer (10 mM, 135 mM) pH 7, containing glucose 11 mM. Platelets were recovered by centrifugation at 200×g for 5 min. After centrifugation, FITC-conjugated goat anti-mouse IgM Fc antibodies, at 1:200 final dilution, in Tris-NaCl buffer (10 mM, 135 mM) pH 7, containing glucose 11 mM, were added to each tube as secondary antibody and the tubes were incubated for 1 h at 37° C. in darkness. At the end of the incubation, the platelets were washed as indicated previously. Finally, the platelets were resuspended in 500 µl of FACS Flow solution (Beckton Dickinson™ Co.) filtered with a 0.22 µm diameter pore Millipore™ filter.

The platelet suspension was analyzed by cytofluorometry in a FACScalibur™ Flow Cytometer equipped with a single 488 nm laser beam (Beckton Dickinson™).

Fluorescence readings were made using the FL-1 channel. The relative size and/or aggregation of platelets was analyzed by diffraction of the laser beam using the FSC channel. Granularity or membranal platelet complexity was analyzed by refraction and reflection of the laser using the SSC channel. Analysis of 10,000 platelets was performed with the following detectors: FSC in E00, in a linear mode with an amplifier gain of 5 V and a detector compensation threshold of 52 V; SSC of 450 V and FL-1 of 700 V, both in logarithmic mode (Baeza et al., op. cit., 1995). The obtained data were analyzed with the Cellquest™ program (Beckton Dickinson™).

Platelets treated as described above, but without any ADP activation, were used as a negative control for the immunoreaction with H308 monoclonal antibody.

Anti-lipidic particle H308 monoclonal antibody showed reactivity with ADP activated platelets. Fluorescence histograms of the immunoreaction of platelets, without any activation or ADP activated, were similar to those presented in: a,m, FIG. 4J, Example 2B, for AC31 patient serum and control serum, respectively. Cytofluorometric histograms showed a 10-fold fluorescence increase when ADP activated platelets were used as antigens, with D=0.50 at $p<0.001$. In addition, graphs showing values of activated membrane platelets complexity and activated platelet aggregation were as shown in: n, FIG. 4K; and n, FIG. 4L for the indicated sera. These results showed higher complexity in ADP activated membrane platelets as well as the lack of platelet aggregation during this process.

These results show clearly the presence of lipidic particles in platelets (which are cellular fragments containing a residual membrane which allows study of the structural and functional characteristics of this cellular organelle).

The methodology of this Example can also be used to detect lipidic particles in isolated cells, such as erythrocytes and leukocytes which are in different physiologic states. These studies will allow characterization of the physiologic states of cells by the quantity of lipidic particles present in their cellular membranes. This knowledge can contribute to maintaining cells in a more appropriate functional state and therefore it can contribute to the prevention of illnesses.

Example 3B

Direct Detection by the Cellular-ELISA Method of Lipidic Particles in Cells from a Subject Using Anti-Lipidic Particle Antibodies from Sera of Patients with Antiphospholipid Syndrome C5337 pancreas cancer cells were used as antigens. $1 \times 10^5$ cells were seeded in each well of a flat-bottom 96-well microtiter plate, which were incubated at 37° C. in an atmosphere containing 5% $CO_2$ until cell confluence in the wells reached 100%. After incubation, 200 ml of a blocking solution containing Tris-NaCl buffer (10 mM, 135 mM) pH 7, and 5% fetal calf serum, was added to each well and the microtiter plates were incubated for 30 min at 37° C. Additionally, the blocking solution was removed and 100 ml of serum from patients with antiphospholipid syndrome, or from healthy blood donors at 1:50 final dilution, using blocking solution, were quickly added to avoid the cell surface becoming dry. All solutions were added subsequently in the same way. After cell cultures were incubated for 30 min at 37° C. in an atmosphere containing 5% $CO_2$, they were washed 3 times with 200 ml of blocking solution for 5 min each wash. Next, 100 ml of peroxidase-conjugated goat anti-human IgG, IgA and IgM Fc antibodies at 1:2000 dilution, in blocking solution, were added as secondary antibody. The microtiter plates were incubated for 30 min at 37° C. in an atmosphere containing 5% $CO_2$. After incubation, microtiter plates were washed as indicated and 100 ml of peroxidase substrate was added to each well and the plates were again incubated for 20 min at 37° C. Finally, 50 ml of 2.5 M sulfuric acid were added to stop the peroxidase reaction and the absorbency was read at 492 nm in an ELISA Labsystems™ reader Multiskan MS™ model.

Sera from the thirty patients studied in Examples 1 and 2B reacted with the neoplastic cells. Arbitrary units higher than 1 were obtained from the 492 nm absorbance readings. To confirm that this immunoreaction was with lipidic particles present in membranes of C5337 pancreas cancer cells, the patient sera were adsorbed with egg-yolk phosphatidylcholine:phosphatidate liposomes (2:1 molar ratio) in Tris-NaCl buffer (10 mM, 1 mM) pH 7, containing 0.1 mmol of phosphatidate, and treated with $CaCl_2$ 5 mM to induce lipidic particle formation. After this adsorption, patient sera no longer reacted with C5337 pancreas cancer cells because the anti-lipidic particle antibodies were eliminated from them.

Figure 7:
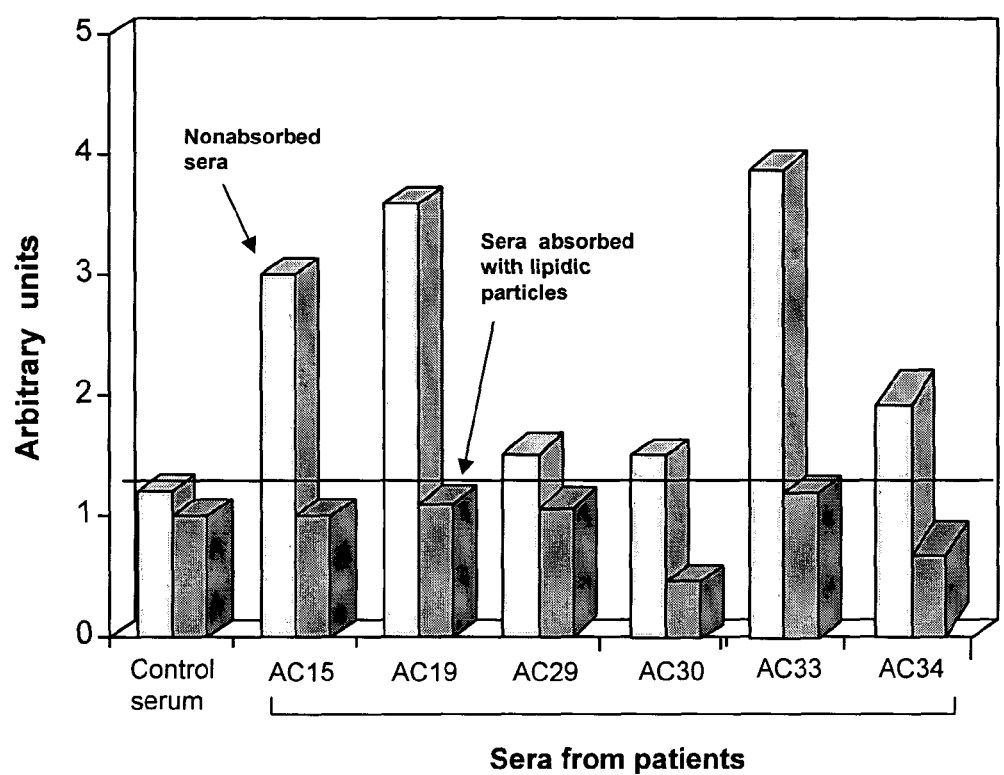
FIG. 7 illustrates analysis by the cellular-ELISA method of the reaction between sera from patients with antiphospholipid syndrome and C5337 human pancreas cancer cells; patient sera were adsorbed with liposomal antigen made from PC:PA (2:1 mole ratio) bearing lipidic particles induced by calcium or not adsorbed.

Results obtained with some patient sera are shown in FIG. 7. These sera are: AC15, AC30 and AC33 from patients with primary antiphospholipid syndrome; AC19 and AC29 from patients with systemic lupus erythematosus, and AC34 from a patient with antiphospholipid syndrome secondary to systemic lupus erythematosus. Bar graphs of the direct reaction of patient sera with C5337 cells as well as of the reaction of patient sera after their adsorption with liposomes bearing lipidic particles are shown in FIG. 7. It can be seen that the reaction of sera with cellular antigens was eliminated after their adsorption with liposomes bearing lipidic particles because the anti-lipidic particle antibodies that they contained were eliminated. C5337 cells were incubated with a serum from a healthy blood donor (FIG. 7) as a negative control for the reaction of human sera with cellular lipidic particles. In FIG. 7, the dark line indicates the upper limit above of which the reactions of sera with cellular antigens are positive.

These experiments are very important because they show that the anti-lipidic particle antibodies in the sera of ill subjects, which were first detected with experimental membrane models such as liposomes, also reacted with the lipidic particles of cellular antigens, which really represent a natural antigen such as those found in humans and animals.

Example 3C

Direct Detection by the Immunofluorescence Method of Lipidic Particles in Cells from a Subject Using Anti-Lipidic Particle Antibodies from the Sera of Patients with Antiphospholipid Syndrome This detection was carried out as indicated in Example 3, with the difference that C5337 pancreas cancer cells were incubated with sera from patients with the antiphospholipid syndrome bearing anti-lipidic particles antibodies instead of the H308 monoclonal antibody. Patient sera were used at 1:50 dilution and FITC-conjugated goat anti-human IgG, IgA and IgM Fc antibodies were used as secondary antibody.

Neoplastic cell cultures were labeled with the anti-lipidic particle antibodies from patient sera in a similar way as described for C5337 pancreas cancer cells in FIG. 6 from Example 3, showing the binding of lipidic particles from neoplastic membranes with these anti-lipidic particle antibodies.

On the other hand, the methodology described in this Example can be applied alternatively to the detection of anti-lipidic particle antibodies in patient sera when these antibodies have not yet been detected by the procedures indicated in the Examples 1 and 2B.

From previous examples, we can conclude that in another favorite modality of the present invention, a diagnostic kit particularly useful for the direct detection of lipidic particles in cellular antigens includes: at least an indicator reagent including at least an anti-lipidic particle monoclonal antibody; at least a buffer solution as a medium to allow the reaction to proceed; and fluorescent or enzymatic procedures to detect this reaction.

In this preferred embodiment of the diagnostic kit, the cell samples from the ill individual are made to react with anti-lipidic particle monoclonal antibody, in other words with the indicator reagent.

In an alternative embodiment of the diagnostic kit, instead of the anti-lipidic particle monoclonal antibody, at least a patient serum in which anti-lipidic particle antibodies can be used as has been previously demonstrated using the methodology described in Examples 1 and 2B.

In an alternative embodiment, the diagnostic kit includes one or more cell culture microtiter plate(s) or centrifuge tube(s) to contain and for the development of the reaction.

In another preferred embodiment of the present invention, a kit for the detection of lipidic particles in cells in different physiologic states from a human or animal subject includes: at least an indicator reagent including at least an anti-lipidic particle monoclonal antibody; at least a buffer solution as a medium to allow the reaction; and fluorescent or enzymatic procedures to detect this reaction.

In this preferred embodiment of the detection kit, cell samples in different physiologic states are made react with the anti-lipidic particle monoclonal antibody, in other words with the indicator reagent.

In an alternative embodiment, the detection kit for lipidic particles in cells in different physiologic states includes one or more cell culture microtiter plate(s) or centrifuge tube(s) to contain and for the development of the reaction.

Example 4

Obtaining Mice that Produce Anti-Lipidic Particle Antibodies by Immunization with Liposomes Bearing Lipidic Particles Induced by Manganese Ten 2-month old BALB/c female mice were immunized by intrasplenic injection of 100 μg of egg-yolk phosphatidylcholine:phosphatidate liposomes (2:1 molar ratio) in Tris-NaCl buffer (10 mM, 1 mM) pH 7, containing 0.1 μmol of phosphatidate and treated with $MnCl_2$ 5 mM to induce lipidic particle formation. Intrasplenic immunization was repeated 2 weeks later by the method described by Nilsson et al. (op. cit. 1987). Additionally, BALB/c female mice were intraperitoneally injected with the same liposome dose 2 weeks later, then they were boosted 4 times at 2-week intervals.

Seven days after the last immunization, female mice were bled from the orbital sinus to analyze the presence of anti-lipidic particle antibodies in serum. Using this immunization procedure, 60% of the immunized BALB/c female mice produced anti-lipidic particle antibodies.

Immunoreaction analysis of mouse serum was performed using the liposomal cytofluorometry method. Egg-yolk phosphatidylcholine:phosphatidate liposomes (2:1 molar ratio) in Tris-NaCl buffer (10 mM, 1 mM) pH 7, containing 0.1 mmol of phosphatidate and treated with 5 mM $MnCl_2$ to induce lipidic particle formation were used as antigens. Analysis of 10,000 liposomes was performed in logarithmic mode with the following detectors: FSC in E00, with a detector compensation threshold of 52V; SSC of 401 V and FL-1 of 748 V (Baeza et al., op. cit., 1995). The obtained data were analyzed with the Cellquest™ program (Beckton Dickinson™).

Autofluorescence and lipidic bilayer complexity (SSC) of liposomes treated with $MnCl_2$ (FIG. 8A) were not modified when these liposomes were also incubated with FITC-conjugated goat anti-mouse IgG, IgA and IgM Fc antibodies as secondary antibody (FIG. 8B) because in the absence of anti-lipidic particle antibodies the secondary antibody does not bind directly to liposomes.

Mice sera were incubated with liposomal antigens and the immunoreaction was detected using FITC-conjugated goat anti-mice IgG, IgA and IgM Fc antibodies as secondary antibody. Sera for analysis were obtained before the mice were immunized as well as after the immunization with liposomal antigens.

Sera from mice before immunization did not show any reaction with lipidic particles since fluorescence and their lipidic bilayer complexity values (SSC) were similar to those of control liposomes that were treated only with manganese (FIG. 8A). Sera were mixed and used as a negative control for the mouse serum immunoreaction with lipidic particles (FIG. 8C).

Figure 8:
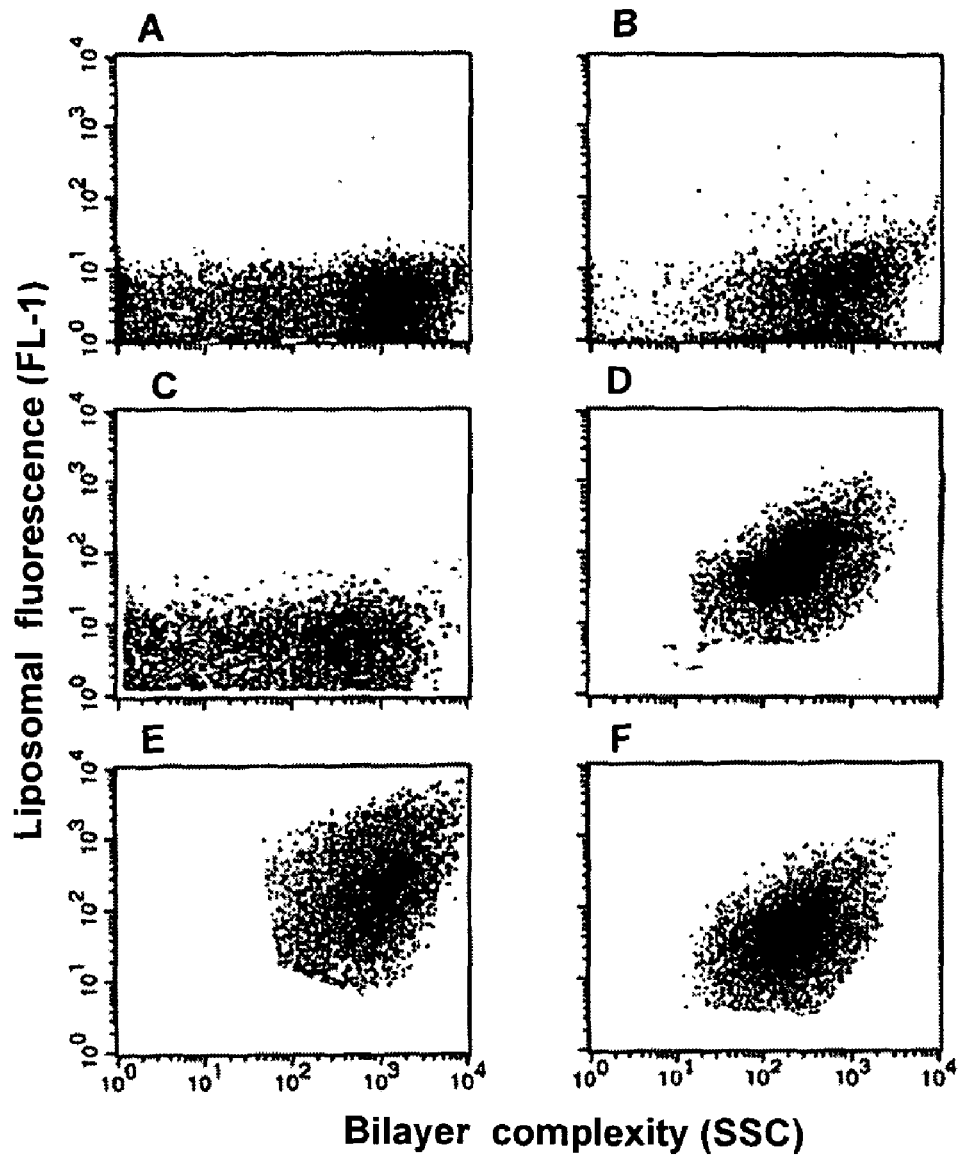
FIGS. 8A-8F show graphs of liposomal fluorescence and liposomal bilayer complexity and analyze the reaction between liposomal antigens and sera from BALB/c mice before or after they were immunized with PC:PA (2:1 mole ratio) liposomes bearing lipidic particles induced by manganese. Liposomal antigens used in the immunoreactions were the same ones used for mouse immunization.

Sera from mice after immunization with liposomal antigens treated with manganese showed an immunoreaction that produced a liposomal fluorescence 10- to 100-fold higher than the reaction of mouse control sera (FIG. 8C), with values of $D \geq 0.5$ at $p<0.001$. As an example, cytofluorometry graphs of the reaction of serum from RB11, RB14 and RB17 mice are shown in FIGS. 8 D, 8E and 8F. Reaction between the antibodies of sera from these mice and lipidic particles, although positive, was different for each serum, with values of $D=0.9$, $D=0.91$ and $D=0.79$, respectively, which can be attributed to the polyclonal origin of these antibodies. SSC values from immunoreaction (FIGS. 8 D, 8E and 8F) were similar to those of control liposomes incubated with manganese (FIG. 8A), and they showed the presence of lipidic particles which give the reaction with the anti-lipidic particle antibodies from mouse sera.

Figure 9:
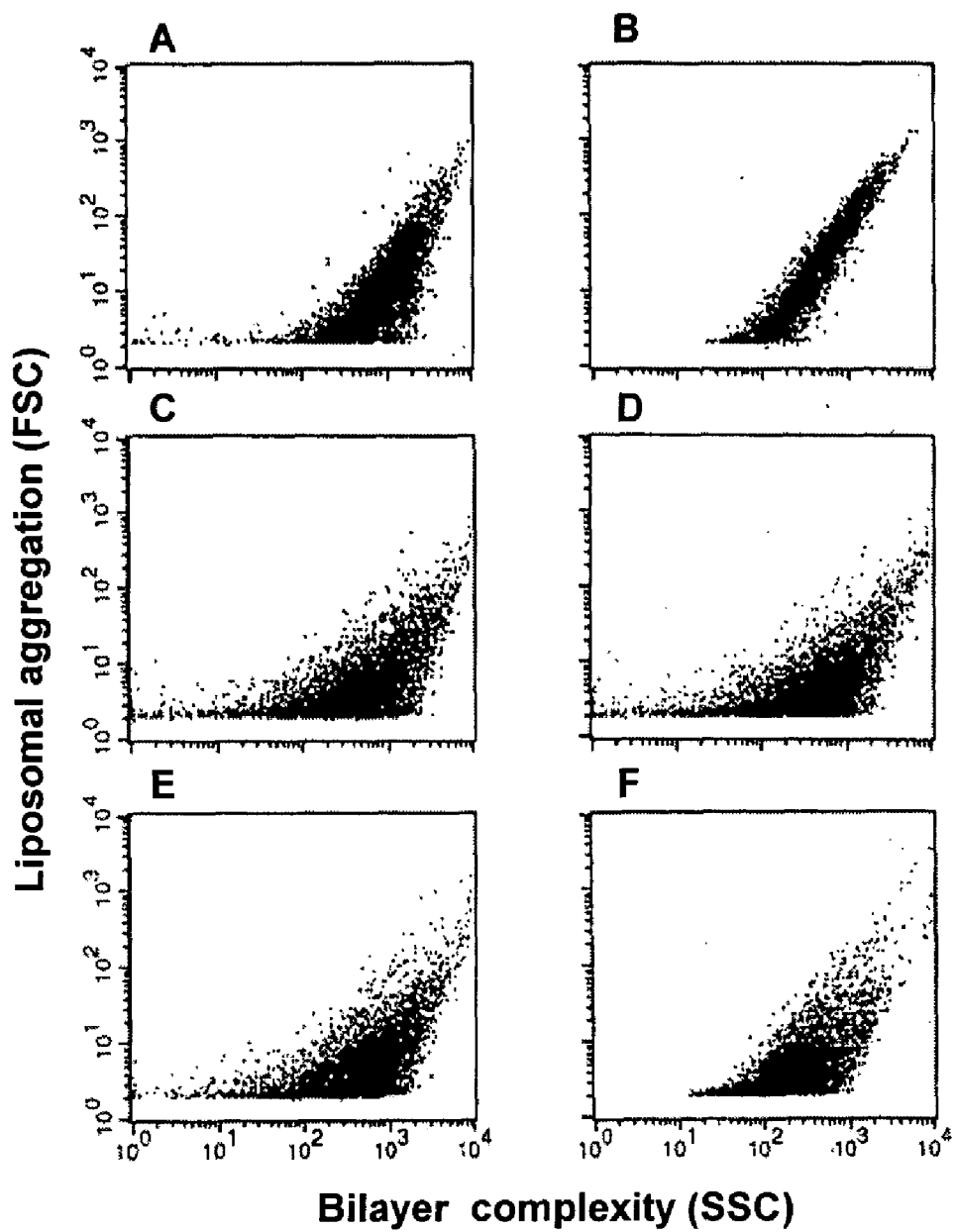
FIGS. 9A-9F show graphs of liposomal aggregation and liposomal bilayer complexity and analyze the reaction between liposomal antigens and sera from BALB/c mice before or after they were immunized with PC:PA (2:1 mole ratio) liposomes bearing lipidic particles induced by manganese. Liposomal antigens used in the immunoreactions were the same ones used for mice immunization.

Furthermore, the reaction of immunized mice sera with lipidic particles did not show any liposomal aggregation, that could increase in unspecific way the fluorescence registered and to give a positive false result, since FSC values after the immunoreaction (FIGS. 9D-9F) were similar to those of liposomes incubated with manganese (FIG. 9A), or with the secondary antibody (FIG. 9B), or with mice sera before the immunization (FIG. 9C). SSC values in FIGS. 9A-9F also showed the presence of lipidic particles in liposomal antigens as described in FIGS. 8A-8F.

In mice immunized with liposomes bearing lipidic particles induced by manganese, after detection of anti-lipidic particle antibodies anti-cardiolipin antibodies, anti-nuclear and anticoagulant antibodies also were detected. These findings confirm our hypothesis which proposes that anti-lipidic particle antibodies constitute the first stage in the development of illnesses associated with antiphospholipid antibodies. The mouse that had the highest reaction with lipidic particles was RB14 with a value of D=0.91, and was used to obtain anti-lipidic particle monoclonal antibodies.

Example 4A

Obtaining Mice that Produce Anti-Lipidic Particle Antibodies by Immunization with Liposomes Bearing Lipidic Particles Induced by Chlorpromazine or Procainamide Ten 2-month old BALB/c female mice were immunized by intrasplenic injection of 100 µg of egg-yolk, phosphatidylcholine:phosphatidate liposomes (2:1 molar ratio) in Tris-NaCl buffer (10 mM, 1 mM) pH 7, containing 0.1 mmol of phosphatidate and treated with the lipidic particle-inducer drug procainamide at a concentration of 8 mM. Immunization was carried out as indicated in Example 4. Seven days after the last immunization, female mice were bled from the orbital sinus to analyze the presence of anti-lipidic particle antibodies in the sera. Using this immunization procedure, 70% of the immunized BALB/c female mice produced anti-lipidic particle antibodies.

Immunoreaction analysis of mouse sera was made by the liposomal cytofluorometry method as indicated in Example 4. Egg-yolk phosphatidylcholine:phosphatidate liposomes (2:1 molar ratio) in Tris-NaCl buffer (10 mM, 1 mM) pH 7, containing 0.1 mmol of phosphatidate and treated with 8 mM procainamide to induce lipidic particles formation were used as antigens. Analysis of 10,000 liposomes was made in logarithmic mode as described in Example 4.

Figure 10:
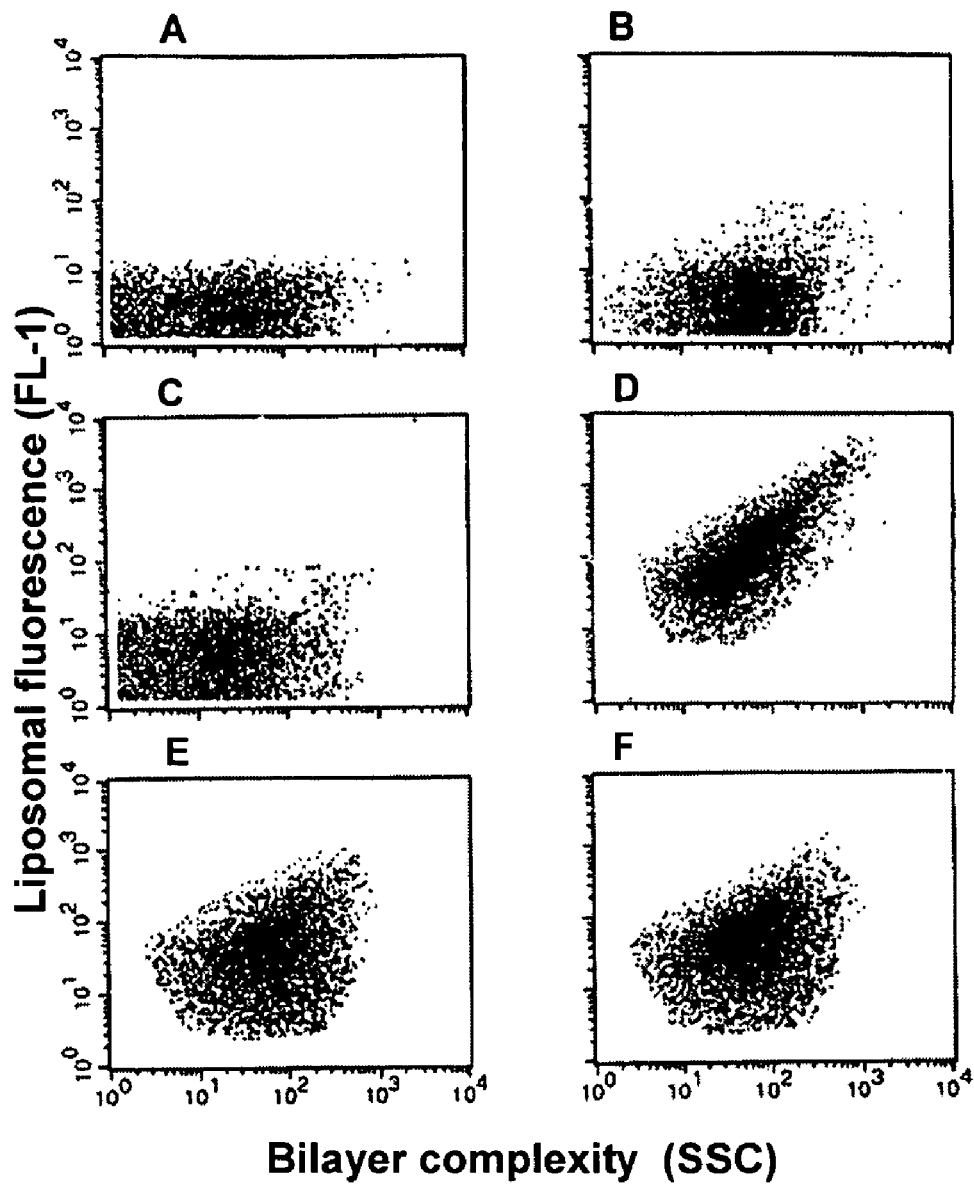
FIGS. 10A-10F show graphs of liposomal fluorescence and liposomal bilayer complexity and analyze the reaction between liposomal antigens and sera from BALB/c mice before or after they were immunized with PC:PA (2:1 mole ratio) liposomes bearing lipidic particles induced by procainamide. Liposomal antigens used in the immunoreactions were the same ones used for mice immunization.

Autofluorescence and lipidic bilayer complexity (SSC) of liposomes treated with procainamide (FIG. 10A) were not modified when these liposomes were also incubated with FITC-conjugated goat anti-mouse IgG, IgA and IgM Fc antibodies as secondary antibody (FIG. 10B), because in the absence of anti-lipidic particle antibodies the secondary antibody does not bind directly to liposomes bearing lipidic particles induced by procainamide.

Mice sera were incubated with liposomal antigens and the immunoreaction detected using FITC-conjugated goat anti-mouse IgG, IgA and IgM Fc antibodies as secondary antibody. Sera for analysis were obtained before the mice were immunized as well as after the immunization with liposomal antigens bearing lipidic particles induced by procainamide.

Sera obtained before the mice were immunized did not show any reaction with lipidic particles, since fluorescence and their lipidic bilayer complexity values (SSC) were similar to those of control liposomes that were treated only with procainamide (FIG. 10A). Sera obtained before mice immunization were mixed and the mixture was used as a negative control for the mouse serum immunoreaction with lipidic particles (FIG. 10C).

Sera obtained after mice were immunized with liposomal antigens treated with the lipidic particle-inducer drug procainamide showed an immunoreaction that produced a liposomal fluorescence 10- to 100-fold higher than the reaction of control mice sera (FIG. 10C), with values of $D \geq 0.5$ at $p<0.001$. As an example, cytofluorometry graphs of the reaction of serum from RF11, RF14 and RF17 mice are showed in FIGS. 10D, 10E and 10F, respectively. Reaction between the antibodies of these mouse sera and lipidic particles, although positive, was different for each serum, with values of D=0.8, D=0.72 and D=0.67, respectively, which can be attributed to the polyclonal origin of these antibodies. SSC values from the immunoreaction (FIGS. 10D, 10E and 10F) were similar to those of control liposomes incubated with procainamide (FIG. 10A), and they showed the presence of lipidic particles in liposomes which react with anti-lipidic particle antibodies from mouse sera.

Furthermore, the reaction of sera from immunized mice did not produce any liposomal aggregation that could nonspecifically increase the fluorescence registered and give a positive false result, since FSC values after the immunoreaction were similar to those of liposomes incubated with procainamide, or with the secondary antibody, or with mouse sera before the immunization in a similar way to that described in FIGS. 9A-9F.

Similar results to those shown in FIGS. 10A-10F were obtained when mice were immunized with liposomes bearing lipidic particles induced by the lipidic particle-inducer drug chlorpromazine at a concentration of 3 mM.

Figure 11:
FIG. 11 is a photograph of a seven (7) month old BALB/c female mouse immunized with PC:PA (2:1 mole ratio) liposomes bearing lipidic particles induced by chlorpromazine. Alopecia and lesions on the face in the form of butterfly wings are observed.

After the detection of anti-lipidic particle antibodies in immunized mice, anti-cardiolipin antibodies, anti-nuclear and anticoagulant antibodies also were detected in them in a similar fashion as described for mice immunized with liposomes treated with manganese in Example 4. These findings corroborate that anti-lipidic particle antibodies constitute the first stage in the development of illnesses associated with antiphospholipid antibodies. Furthermore, in mice immunized with liposomes incubated with procainamide or chlorpromazine the presence of deposits of immune complexes have been demonstrated in different organs. In addition, these mice developed alopecia and lesions on the face in the form of butterfly wings similar to those that have been described in human systemic lupus erythematosus. FIG. 11 shows the picture of a 7-month-old BALB/c female mouse that was treated with liposomes bearing lipidic particles induced by chlorpromazine, where alopecia and lesions in the face in the form of butterfly wings can be observed.

This animal model indicates that antigens bearing lipidic particles induced by chlorpromazine or procainamide were more efficient in causing not only anti-lipidic particles antibodies in BALB/c female mice, but also a pathology that is more similar to the one that is presented in humans.

Example 4B

Obtaining Mice that Produce Anti-Lipidic Particle Antibodies by Immunization with the Drugs Chlorpromazine or Procainamide For this treatment, the immunization procedure indicated in Example 4A was modified since chlorpromazine or procainamide drug was administered directly in the absence of liposomal antigens to BALB/c female mice.

Ten 2-month-old BALB/c female mice were immunized by intramuscular injection of the lipidic particle-inducer drugs chlorpromazine or procainamide, using 3 mg/Kg of body weight for chlorpromazine and 10 mg/Kg of body weight for procainamide, each 24 hs, for 2 months. Drug doses were similar to those that are administered in the medical treatment of humans for psychotic and mania dysfunctions for chlorpromazine and for the treatment of cardiac arrhythmias for procainamide.

Seven days after the last intramuscular injection, female mice were bled from the orbital sinus to analyze the presence of anti-lipidic particle antibodies in the sera. Using this immunization procedure, 50% of the immunized BALB/c female mice produced anti-lipidic particle antibodies.

Immunoreaction analysis of the mice sera was performed by the liposomal cytofluorometry method as indicated in Example 4. Egg-yolk phosphatidylcholine:phosphatidate liposomes (2:1 molar ratio) in Tris-NaCl buffer (10 mM, 1 mM) pH 7, containing 0.1 mmol of phosphatidate and treated with 8 mM procainamide to induce lipidic particle formation were used as antigens. Analysis of 10,000 liposomes was made in the logarithmic mode as described in Example 4.

Mice sera were incubated with liposomal antigens and the immunoreaction was detected using FITC-conjugated goat anti-mouse IgG, IgA and IgM Fc antibodies as secondary antibody. Sera for analysis were obtained before mice were treated with the lipidic particle-inducer drug as well as after of these treatments.

Sera obtained from mice after they were treated with the lipidic particle-inducer drug procainamide showed an immunoreaction that produced a liposomal fluorescence 4-fold higher than the reaction of mice sera before treatment (a, FIGS. 12 A, D, and G), with values of D≧0.5 at p<0.001. As an example, cytofluorometry graphs of the reaction of serum from RP37, RP38 and RP39 mice are shown in: b, FIG. 12 A; g, FIG. 12 D; and j, FIG. 12 G. Reaction between the antibodies of sera from these mice and lipidic particles, although positive, was different for each serum, with values of D=0.58, D=0.68 and D=0.8, respectively, which can be attributed to the polyclonal origin of these antibodies. SSC values from immunoreaction shown in: d, FIG. 12 B; h, FIG. 12E; and k, FIG. 12H were similar to those of control liposomes incubated with procainamide (FIG. 10A), and they showed the presence of lipidic particles which react with the anti-lipidic particle antibodies from mice sera.

Figure 12:
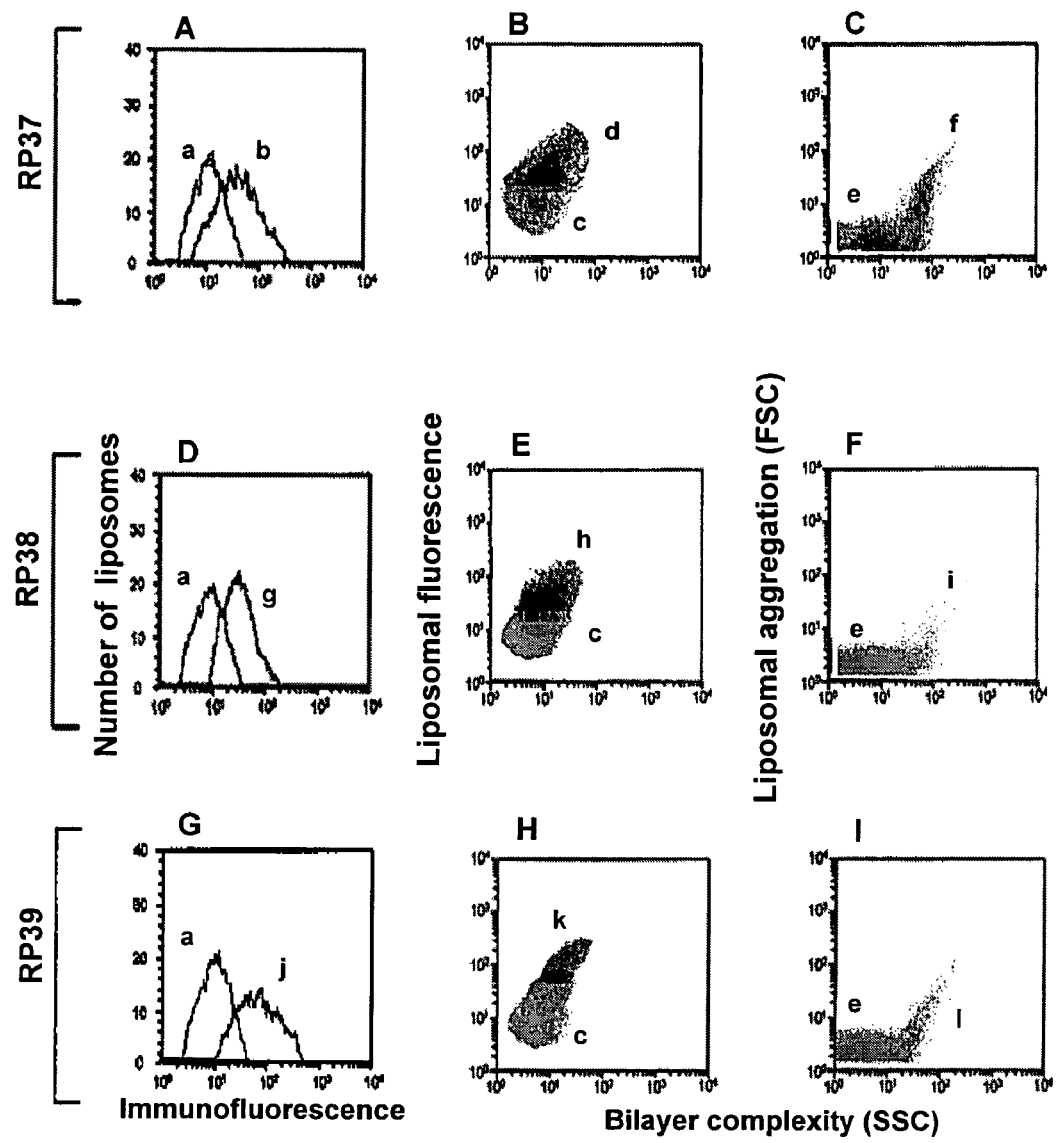
FIGS. 12A-12I are cytofluorometric analyses of the reaction between liposomal antigens and sera from BALB/c mice before or after the mice were treated by intramuscular injection each 24 hours for two months with 3 mg/Kg of body weight of the lipidic particle-inducer drug procainamide. Liposomal antigens used in the immunoreactions were made from PC:PA (2:1 mole ratio) bearing lipidic particles induced by procainamide.

Furthermore, the reaction of immunized mice sera with lipidic particles did not show any liposomal aggregation, since FSC values after the immunoreaction (f, FIG. 12C; i, FIGS. 12 F; and l, FIG. 12 I) were similar to those of liposomes incubated with manganese (FIG. 9, Example 4) or with mice sera before mice were treated with the lipidic particle-inducer drug procainamide (e, FIGS. 12C, F and I).

Anti-lipidic particle antibodies also were detected before anti-cardiolipin antibodies, anti-nuclear and anticoagulant antibodies in these mice, in a similar way as described for mice in Examples 4 and 4A. Furthermore, the presence of deposits of immune complexes in different organs and the development of alopecia and lesions in the face in the form of butterfly wings also occurred in these mice.

Similar results to those shown in FIGS. 12A-12I were obtained when BALB/c female mice were treated with the lipidic particle-inducer drug chlorpromazine.

These results indicate that the lipidic particle-inducer drugs chlorpromazine or procainamide induce the formation of lipidic particles in the membranes of mice cells which subsequently induce the production of anti-lipidic particle antibodies and the development of a pathology similar to the human antiphospholipid syndrome secondary to systemic lupus erythematosus. The formation of lipidic particles by the lipidic particle-inducer drugs chlorpromazine or procainamide in liposomes has been previously demonstrated by nuclear magnetic resonance (Baeza et al., op. cit., 1995; Aguilar, op. cit., 1997; Aguilar et al., op. cit., 1999).

Example 4C

Obtaining Anti-Lipidic Particle Antibody-Producing Mice by Passive Immunization with the Anti-Lipidic Particle H308 Monoclonal Antibody For this treatment, the immunization procedure indicated in Example 4 was modified since passive immunization of BALB/c female mice was carried out.

Ten 2-month old BALB/c female mice were immunized by intraperitoneal injection of 1 μg of anti-lipidic particle H308 monoclonal antibody each week for 2 months. Seven days after the last intraperitoneal injection, female mice were bled from the orbital sinus to analyze for the presence of anti-lipidic particle antibodies in the sera. Using this immunization procedure, 80% of the immunized BALB/c female mice produced anti-lipidic particle antibodies.

Immunoreaction analysis of mice sera was performed using the liposomal cytofluorometry method as indicated in Example 4. Egg-yolk phosphatidylcholine:phosphatidate liposomes (2:1 molar ratio) in Tris-NaCl buffer (10 mM, 1 mM) pH 7, containing 0.1 μmol of phosphatidate and treated with 5 mM $CaCl_2$ to induce lipidic particle formation were used as antigens. Analysis of 10,000 liposomes was made in logarithmic mode as described in Example 4.

Mice sera were incubated with liposomal antigens and the immunoreaction were detected using FITC-conjugated goat anti-mouse IgG, IgA and IgM Fc antibodies as secondary antibody. Sera for analysis were obtained before mice were treated by passive immunization with the anti-lipidic particle H308 monoclonal antibody as well as after mice received this immunization.

Sera obtained after mice were treated by passive immunization with the anti-lipidic particle H308 monoclonal antibody showed the presence of anti-lipidic particle antibodies in them since cytofluorometry graphs of the reaction of passive immune mice sera with liposomes bearing lipidic particles induced by $CaCl_2$ were similar to those described in FIGS. 8, 9, 10 and 12 (which showed anti-lipidic particle antibodies induced by different antigens containing lipidic particles).

Anti-lipidic particle antibodies also were detected before anti-cardiolipin antibodies, anti-nuclear and anticoagulant antibodies in these mice, in a similar way as described for mice in Examples 4, 4A, and 4B. Additionally, the presence of deposits of immune complexes in different organs and the development of alopecia and lesions in the face in the form of butterfly wings also occurred in these mice.

These results showed the direct participation of anti-lipidic particle antibodies in the development in BALB/c female mice of a pathology similar to human antiphospholipid syndrome secondary to systemic lupus erythematosus. Therefore, a possible treatment of these illnesses would be to inhibit anti-lipidic particle antibodies and/or to stabilize cellular membranes that prevent the formation of lipidic particles, as subsequently described.

Example 5

Obtaining Hybridomas by Fusion of P3X63Ag8U.1 Cells with Spleen Cells of an Anti-Lipidic Particle Antibody-Producing Balb/c Female Mouse Four days before the planned fusion, three mice previously immunized by intrasplenic and intraperitoneal injection of 100 μl of egg-yolk phosphatidylcholine:phosphatidate liposomes (2:1 molar ratio) in Tris-NaCl buffer (10 mM, 1 mM) pH 7, containing 0.1 μmol of phosphatidate and treated with 5 mM $MnCl_2$ to induce lipidic particles formation were boosted by intravenous tail vein injection using the same liposome dose. The rational way is to initiate secondary immune responses selectively in the spleen as opposed to lymph nodes. Therefore the mouse producing the highest titer of anti-lipidic particle antibodies was chosen for hybridoma production.

The spleen of the RB14 BALB/c female mouse producing the highest titers of anti-lipidic particle antibodies was removed under sterile conditions and placed in a petri dish with 6 ml of incomplete DMEM cell culture medium. The mouse spleen was dispersed until a suspension of single cells was obtained using blunt tipped pincers. The cellular suspension was transferred to a 15-ml Falcon™ tube and left in repose to allow the thick residuals to settle. Next, cellular suspension was transferred to another Falcon™ tube and centrifuged at 17×g for 7 min. Subsequently, the supernatant was decanted and the cellular pellet was resuspended by agitation and the cellular suspension was diluted by addition, drop by drop, of 10 ml of incomplete DMEM cell culture medium. The cellular suspension was centrifuged as indicated above, then the supernatant was decanted and 4 ml of 0.16 M $NH_4Cl$ was added for erythrocyte lysis. In this step, the tube containing the cellular suspension was incubated at 37° C. and gently rotated for 4 min. Later, 6 ml of incomplete DMEM cell culture medium was added and the cellular suspension was centrifuged at 17×g for 7 min. After centrifugation, the supernatant was decanted and the cellular pellet was gently resuspended in 10 ml of incomplete DMEM cell culture and was allowed to stand at room temperature until use (Köhler and Milstein, 1975. Nature 256:495.497).

On the other hand, P3x63Ag8U.1 myeloma cells were collected from cell culture plates and transferred to Falcon™ tubes. Aliquots from P3x63Ag8U.1 myeloma cells and mouse spleen cells were treated with trypan blue and counted using a Neubauer™ camera. The viability of both cellular suspensions were higher than 95%. P3x63Ag8U.1 myeloma cells and mouse spleen cells were mixed in a 1:1 cellular proportion, using 36×10$^6$ cells of each cellular type, and then the cellular mixture was washed with 10 ml of incomplete DMEM cell culture medium. After centrifugation at 17×g for 5 min, the supernatant was decanted and the cellular pellet was gently resuspended. Subsequently, 1 ml of polyethyleneglycol 4000 solution was added drop by drop, over 1 min, and the mixture was manually shaken for 1.5 min, then 1 ml of incomplete DMEM cell culture medium was added for 30 sec with slow tube rotation. Next, 3 ml of incomplete DMEM cell culture medium was added for 30 sec, also with slow tube rotation, and then 16 ml of the same medium was added for 1.5 min with gentle agitation. Finally the volume of the fused cell suspension was brought up to 40 ml with incomplete DMEM cell culture medium and the fused cell suspension was incubated without agitation for 5 min at room temperature. Later on, the fused cell suspension was centrifuged at 17×g for 5 min, the supernatant was decanted and the fused cell pellet was washed again with 40 ml of incomplete DMEM medium. The fused cell pellet was resuspended in 30 ml of selection DMEM-HAT medium and aliquots of 100 ml of this fused cell suspension were seeded in the wells of three 96-well flat-bottom microtiter plates which 24 hs before cell fusion were seeded with macrophages as feeder cells. The microtiter plates were incubated at 37° C., in an atmosphere with 5% $CO_2$. After five or eight days, the cellular fusion hybridomas were fed with 50 ml of selection DMEM-HAT medium and finally after 11 days, the cellular fusion hybridoma supernatants were changed for 100 ml of DMEM-HAT media.

After hybridoma growth, the supernatants were screened by the liposomal-ELISA method in order to detect the production of anti-lipidic particle antibodies by them. Cellular samples from all hybridomas producing anti-lipidic particle monoclonal antibodies were frozen at −70° C. in liquid nitrogen. Later, 10 hybridomas with high anti-lipidic particle monoclonal antibody titers were chosen (Table 3) and they were cloned again by limiting dilution in 96-well flat-bottom microtiter plates. After hybridoma growth supernatants were screened again by the liposomal-ELISA method and those producing the higher titers of anti-lipidic particle monoclonal antibodies were cultivated in 250 ml bottles to obtain large amounts of supernatants containing these antibodies.

TABLE 3

Hybridomas producing anti-lipidic particles antibodies.

| Hybridoma | Arbitrary Units | Hybridoma | Arbitrary Units |
|---|---|---|---|
| H40 | 26 | H120 | 36 |
| H65 | 32 | H121 | 35 |
| H70 | 3 | H176 | 42 |
| H90 | 22 | H200 | 30 |
| H110 | 23 | H308 | 48 |

Example 6

Detection of the Inhibition of Anti-Lipidic Particle H308 Monoclonal Antibody Using Phosphorylated Haptens by the Liposomal-ELISA Method Costar™ microtiter plates, with 96 flat-bottom wells with a high lipidic antigen binding property (Costar™ Co. Cambrige, USA) were coated by adding to each well 100 μl of liposomes made from egg-yolk phosphatidylcholine:phosphatidate (2:1 molar ratio) in Tris-NaCl buffer (10 mM, 1 mM) pH 7, containing 0.1 μmol of phosphatidate and treated with 5 mM $CaCl_2$ to induce lipidic particle formation. The microtiter plates were incubated at room temperature for 1 h and blocked for 1 h at room temperature in a similar way as was described in Example 1. Next, the blocking solution was discarded by suction and 100 ml of H308 monoclonal antibody that was previously incubated with the phosphorylated haptens was added immediately to each well, avoiding their becoming dry.

Phosphorylcholine, glycerolphosphorylcholine, phosphorylserine, glycerol-phosphorylserine and phosphorylethanolamine were used as haptens in quantities of 0.2, 0.4, 0.6, 0.8 and 1.0 mmol. The chemical structure of these haptens is presented in FIG. 13. Phosphorylcholine and glycerolphosphorylcholine constitute part of the polar region of the lipid phosphatidylcholine; phosphorylserine and glycerolphosphorylserine constitute part of the polar region of phosphatidylserine; and phosphorylethanolamine is part of phosphatidylethanolamine.

Aliquots of 100 ml of H308 monoclonal antibody were incubated with 100 ml of each one of the hapten solutions for 30 min at 30° C. Later on, the liposomal-ELISA method was applied as described in Example 1. Peroxidase-conjugated goat anti-mouse IgM Fc antibodies were used as secondary antibody.

When phosphorylcholine was used as a hapten to block H308 monoclonal antibody, a decrease in the immunoreaction of this antibody with liposomal antigen bearing lipidic particles was observed. This decrease gave an absorbance at 492 nm of 0.06, with 0.6 mmoles of hapten (E, FIG. 14) which represents a 82% inhibition in immunoreaction compared to reaction in the absence of hapten (A, FIG. 14). With 0.2 mmoles of glycerol-phosphorylcholine, an 100% inhibition of H308 monoclonal antibody was shown (F, FIG. 14). On the other hand, glycerolphosphorylserine (B, FIG. 14), phosphorylserine (C, FIG. 14) and phosphorylethanolamine (D, FIG. 14) do not cause any inhibition of H308 monoclonal antibody reaction with lipidic particles in liposomes.

Figure 13:
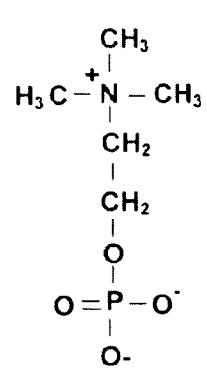
FIG. 13 illustrates the chemical structure of phosphorylcholine, glycerolphosphorylcholine, phosphoryl-serine, glycerolphosphorylserine and phosphorylethanolamine, which are used as haptens in the inhibition of anti-lipidic particle antibodies.
Figure 13:
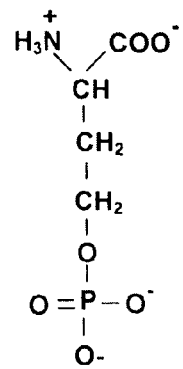
Figure 13:
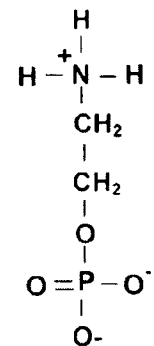
Figure 13:
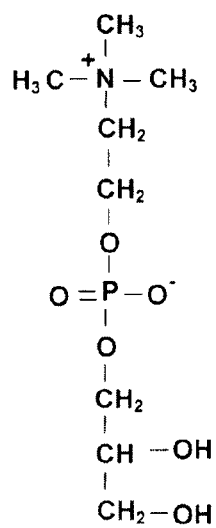
Figure 13:
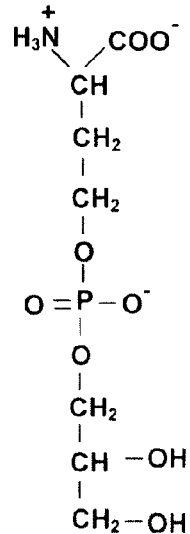

Inhibition of the H308 monoclonal antibody reaction with phosphorylcholine and glycerolphosphorylcholine indicates that the antigen recognition domain of the H308 monoclonal antibody has subdomains that recognize specifically the choline methyl groups lacking in ethanolamine and serine (FIG. 13). In addition the, total inhibition of immunoreaction attained by glycerolphosphorylcholine suggests that the antigen domain recognized by the H308 monoclonal antibody includes chemical groups of glycerol. These findings are in agreement with the structural pattern proposed for the lipidic particle (Cullis et al., op. cit., 1991) (FIG. 15) where monolayer lipids (C, FIG. 15) that form the molecular arrangement different from bilayer (B, FIG. 15) are more separate than lipids that constitute a normal monolayer (A, FIG. 15). In an open monolayer (C, FIG. 15) glycerolphosphorylcholine is more exposed than in a normal bilayer, therefore this is the region in which the H308 monoclonal antibody reacts.

Figure 14:
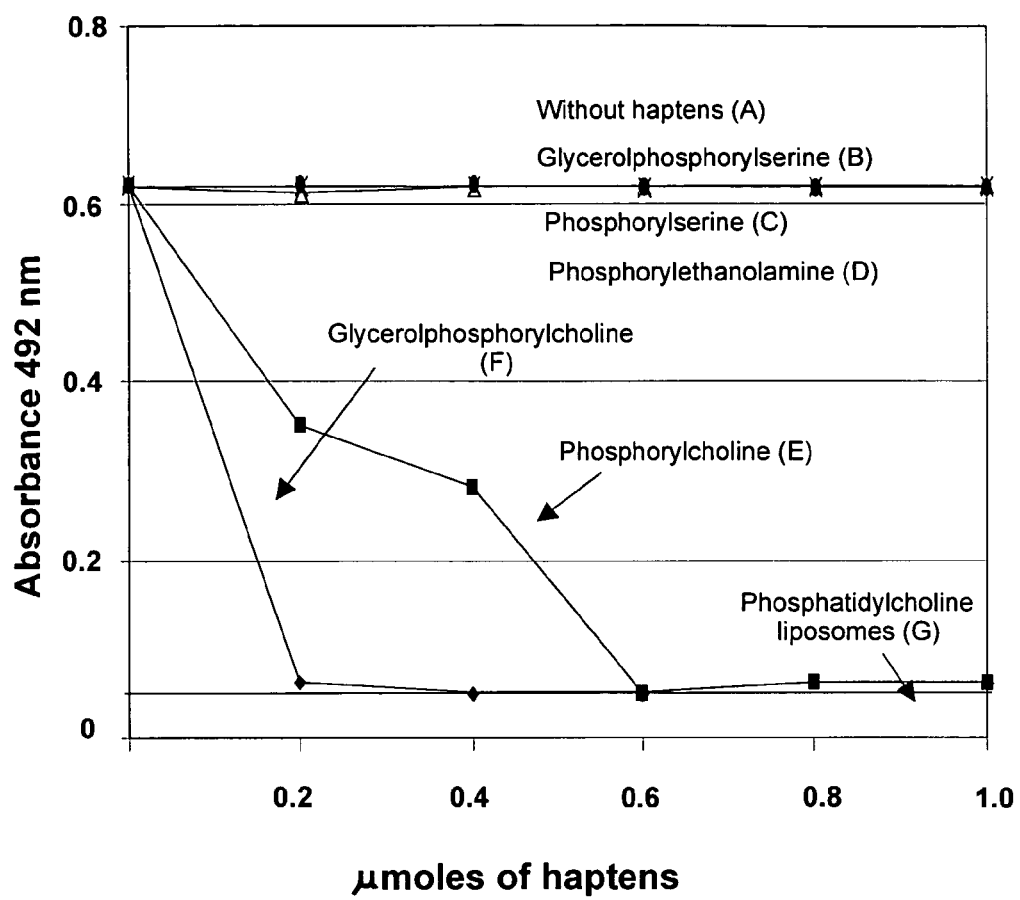
FIG. 14 is a graph of the inhibition of H308 monoclonal antibody by phosphorylcholine, glycerolphosphorylcholine, phosphorylserine, glycerolphosphorylserine or phosphorylethanolamine haptens. Furthermore, the reaction of H308 monoclonal antibody with liposomes made from phosphorylcholine is also shown.
Figure 15:
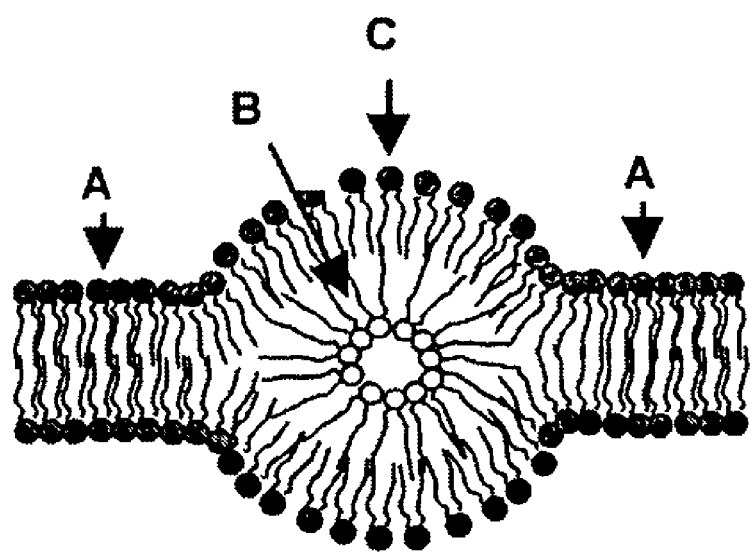
FIG. 15 is a schematic diagram of lipids associated as a bilayer molecular arrangement and an inverted micelle which is inserted in an open lipidic bilayer, which constitutes the lipidic particle as a whole. Arrows indicate the different molecular arrangements adopted by the lipids.

Possibly the central domain of lipidic particle, the region that is observed as an inverted micelle in B, FIG. 15, is formed by conic shaped lipids such as phosphatidate. In contrast, monolayers most open compared to a normal monolayer would be formed by phosphatidylcholine and they would be the regions that the H308 monoclonal antibody identifies. If H308 monoclonal antibody reacts specifically with a phosphatidyl-choline open monolayer, is clear that this antibody does not show any immunoreaction with liposomes formed exclusively by phosphatidylcholine (G, FIG. 14), because in these liposomes the lipids are in a normal monolayer association that constitute the bilayer, in consequence no immunoreaction with H308 monoclonal antibody is detected.

Example 6A

Detection by the Liposomal-ELISA Method of Glycerolphosphorylcholine Hapten Inhibition of Anti-Lipidic Particle Antibodies from Sera of Patients with Antiphospholipid Syndrome Costar™ microtiter plates, with 96 flat-bottom wells with a high lipidic antigen binding property (Costar™ Co. Cambrige, USA) were coated by the addition to each well of 100 ml of liposomes made from egg-yolk phosphatidylcholine:phosphatidate (2:1 molar ratio) in Tris-NaCl buffer (10 mM, 1 mM) pH 7, containing 0.1 mmol of phosphatidate, and treated with 5 mM $CaCl_2$ to induce lipidic particle formation.

Aliquots of 100 ml of the patient sera that were analyzed in Examples 1 and 2B were incubated with 100 ml of 0.2 mmolar glycerophosphorylcholine for 30 min at 30° C. Later on, the blocked patient sera were added to the wells of the microtiter plate and the liposomal-ELISA method was applied as described in Example 1. Peroxidase-conjugated goat anti-human IgG, IgA and IgM Fc antibodies were used as secondary antibody.

Glycerolphosphorylcholine hapten at a concentration of 0.2 mmoles produce an 100% inhibition in the immunoreaction of patient sera with lipidic particles in liposomes, in a similar way as described for the inhibition of H308 monoclonal antibody in FIG. 14, Example 6.

These results confirm that sera from patients with antiphospholipid syndrome have anti-lipidic particle antibodies with an antigenic specificity similar to that of the H308 monoclonal antibody, since they were inhibited in the same proportion by the glycerolphosphorylcholine hapten.

Studies in BALB/c female mice which were simultaneously administered the H308 monoclonal antibody (which developed a pathology similar to human antiphospholipid syndrome as described in Example 4C) and the glycerolphosphorylcholine hapten, showed a blockage in the development of the pathology in BALB/c female mice. H308 monoclonal antibody was administered by intraperitoneal injection of 1 mg each week over two months to BALB/c female mice and simultaneously the glycerolphosphorylcholine hapten was administered at 2.5 mg/Kg of body weight by intravenous injection each 24 hs for 2 months. With this treatment 40% the development of mice pathology was inhibited by H308 monoclonal antibody.

In accordance with the above-mentioned studies, the therapeutically effective quantity of the inhibitor drug glycerolphosphorylcholine is of 2.5 mg/Kg of body weight.

Example 7

Study by the Liposomal Cytofluorometry Method of the Stabilization of Liposomal Membranes that Prevent the Formation of Lipidic Particles and the Subsequent Binding of Anti-Lipidic Particle Antibodies These studies were carried out with a modification in the liposomal cytofluorometry method with liposomes made from egg-yolk phosphatidylcholine:phosphatidate (2:1 molar ratio) in Tris-NaCl buffer (10 mM, 1 mM) pH 7, containing 0.1 mmol of phosphatidate and treated with 0.2 mM chlorpromazine to induce lipidic particle formation, as antigens.

Immediately after the addition of the lipidic particle-inducer drug chlorpromazine, liposomes were incubated with different concentrations of the lipid bilayer stabilizer drugs spermidine or chloroquine. Liposomal preparations were incubated for 30 min at room temperature and were used as antigens. The reaction of these stabilized liposomes with H308 monoclonal antibody was analyzed by the liposomal cytofluorometry method as described in Example 2A, in a FACSCalibur™ Flow Cytometer equipped with a single 488 nm argon laser beam (Beckton Dickinson™).

The relative size and/or liposomal aggregation were analyzed using the FSC channel and the granularity or liposomal bilayers complexity using the SSC channel. Analysis of 10,000 liposomes was made in a logarithmic mode with the following detectors: FSC in E00, with a detector compensation threshold of 52 V and SSC of 401 V (Baeza et al., op. cit., 1995). The obtained data were analyzed with the Cellquest™ program (Beckton Dickinson™).

Figure 16:
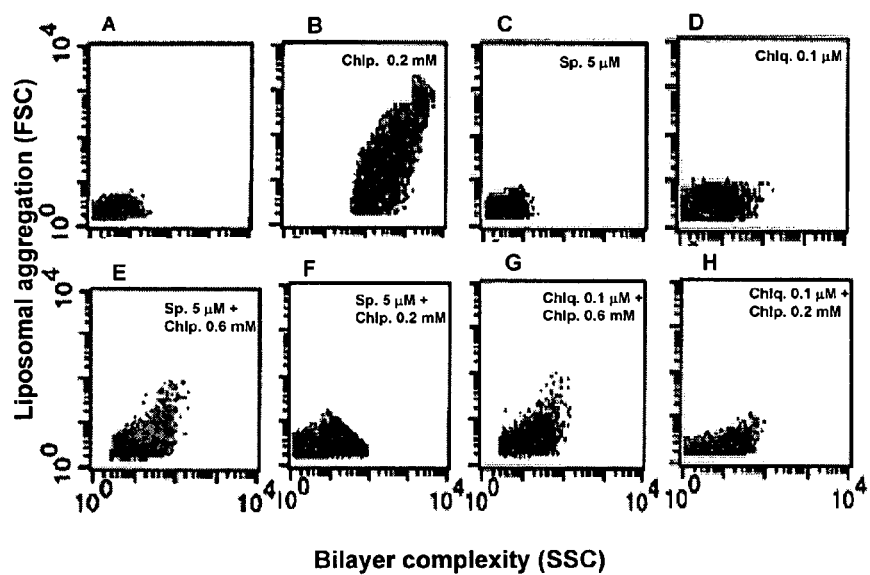
FIGS. 16A-16H are graphs of liposomal aggregation and liposomal bilayer complexity and analyze the lipidic bilayer stabilization of liposomal antigens made from PC:PA (2:1 mole ratio) treated with the lipidic particle-inducer drugs chlorpromazine or procainamide and/or with the lipidic bilayer-stabilizer drugs chloroquine or spermidine.

When egg-yolk phosphatidylcholine:phosphatidate (2:1 molar ratio) liposomes in Tris-NaCl buffer (10 mM, 1 mM) pH 7, and containing 0.1 mmol of phosphatidate (A, FIG. 16), were treated with 0.2 mM chlorpromazine, a 100-fold increase in SSC and FSC values were observed, which showed the presence of lipidic particles and liposomal aggregation, respectively (B, FIG. 16).

In contrast, the incubation of egg-yolk phosphatidylcholine:phosphatidate (2:1 mmolar ratio) liposomes, in Tris-NaCl buffer (10 mM, 1 mM) pH 7, and containing 0.1 mmol of phosphatidate with the stabilizer drugs spermidine (C, FIG. 16) or chloroquine (D, FIG. 16), do not produce any change in liposomal aggregation or liposomal bilayer complexity because the graphs obtained were similar to that corresponding to liposomes in buffer solution (A, FIG. 16). However, when liposomes were incubated simultaneously with the lipidic particle-inducer drug chlorpromazine and the lipidic bilayer stabilizer drugs spermidine (E, F, FIG. 16) or chloroquine (G, H, FIG. 16) there was no lipidic particle formation or liposomal aggregation. It can be observed that SSC and FSC values (E-H, FIG. 16) were very similar to those of liposomes in buffer solution, which showed SSC values smaller than 100 units; contrary to the graph that indicates the presence of lipidic particles, with SSC values higher than 1000 units (B, FIG. 16).

These studies showed that spermidine is effective in stabilizing lipidic bilayers at a concentration of 5 mM, this spermidine quantity blocking the formation of lipidic particles induced by chlorpromazine at concentrations of 0.2 mM and 0.6 mM, respectively (E, F, FIG. 16). For chloroquine, effective concentrations were even smaller, since this stabilizer drug produced liposomal stabilization at a concentration of 0.1 mM when the lipidic particle-inducer drug chlorpromazine were used at 0.2 mM and 0.6 mM, respectively (G, H, FIG. 16).

When liposomes incubated with both drugs (the lipidic particles inducer drug and the lipidic bilayer stabilizer drug) were used as antigens, there was not any immunoreaction with the H308 monoclonal antibody, because the cytofluorometry graphs obtained were as those corresponding to liposomes alone and in absence of antibodies as shown in g, FIG. 3D and i, FIG. 3E, instead of like those that show the reaction of H308 monoclonal antibody with lipidic particles in b, FIG. 3A and d, FIG. 3B.

These results indicate that liposomal membranes were stabilized by interaction with lipidic bilayer stabilizers drugs spermidine or chloroquine and in consequence they do not contain lipidic particles and therefore they do not react with H308 monoclonal antibody.

Example 7A

Study by the Cytofluorometry Method of Cellular Membranes Stabilization that Prevents the Formation of Lipidic Particles and the Later Binding of Anti-Lipidic Particle Antibodies Ag4 mouse myeloma cells suspended in Tris-NaCl buffer (10 mM, 135 mM) pH 7, containing glucose 11 mM, were incubated with the lipidic particle-inducer drug chlorpromazine at 0.2 mM. Immediately after the addition of chlorpromazine, the Ag4 mouse myeloma cells were incubated with different concentrations of the lipid bilayer stabilizer drugs spermidine or chloroquine for 30 min at room temperature. The reaction of these stabilized Ag4 mouse myeloma cells with H308 monoclonal antibody was analyzed by the cytofluorometry method in a FACSCalibur™ Flow Cytometer equipped with a single 488 nm argon laser beam (Beckton Dickinson™).

The relative size and/or Ag4 mouse myeloma cell aggregation were analyzed using the FSC channel and the granularity or cellular membrane complexity using the SSC channel. Analysis of 10,000 Ag8 mouse myeloma cells was made with the following detectors: FSC in E00 in lineal mode with an amplifier gain of 2 V, with a detector compensation threshold of 52 V, and SSC of 250 V. The obtained data were analyzed with the Cellquest™ program (Beckton Dickinson™).

Results obtained with Ag4 mouse myeloma cells incubated with the lipidic particle-inducer drug chlorpromazine and the lipid bilayer stabilizer drugs spermidine or chloroquine were similar to those described in FIG. 16. These results showed that Ag4 cellular membranes were stabilized by interaction with lipidic bilayer stabilizer drugs spermidine or chloroquine and in consequence they do not develop lipidic particles with chlorpromazine.

When Ag4 mouse myeloma cells incubated with both drugs (the lipidic particles inducer drug and the lipidic bilayer stabilizer drug) were used as antigens, there was not any immunoreaction with the H308 monoclonal antibody, in a similar way as demonstrated for liposomes stabilized with the drugs spermidine or chloroquine in Example 7.

These results indicate that cellular membranes of Ag4 mouse myeloma cells, stabilized by their interaction with spermidine or chloroquine, do not develop lipidic particles and therefore they do not react with the H308 monoclonal antibody.

Example 7B

Detection of Lipidic Particles Reversion by the Lipidic Bilayer Stabilizer Drugs Spermidine and Chloroquine Examples 7 and 7A were repeated using as antigens egg-yolk phosphatidylcholine:phosphatidate (2:1 molar ratio) liposomes, in Tris-NaCl buffer (10 mM, 1 mM) pH 7, and containing 0.1 mmol of phosphatidate or Ag4 mouse myeloma cells. The liposomal or cellular antigens were incubated with the lipidic particle-inducer drug chlorpromazine 0.2 mM for 30 min at room temperature before treatment with the lipidic bilayer stabilizer drugs spermidine or chloroquine. Stabilizer drugs were used at the concentrations used in Example 7A.

Cytofluorometric analysis showed that the formation of lipidic particles and the liposomal or cellular aggregation caused by chlorpromazine, which produce data similar to B, FIG. 16, were reversed by the lipid bilayer stabilizers spermidine or chloroquine. This reversion, which destroys lipidic particles in liposomal and cellular antigens, produces data as those shown in E, F, G, and H, FIG. 16, which show lipids in bilayer molecular arrangements.

After lipidic particle reversion, liposomal or cellular antigens do not show any reaction with H308 monoclonal antibody, due to the absence of lipidic particles in their surfaces.

These experiments showed that spermidine and chloroquine have the action of preventing the formation of lipidic particles and additionally they can also destroy lipidic particles already formed. These findings are very important for the application of these stabilizer drugs in the treatment of human illnesses in which lipidic particles and/or anti-lipidic particle antibodies participate.

Studies in BALB/c female mice which were simultaneously administered the H308 monoclonal antibody (which develop in these mice a pathology similar to human antiphospholipid syndrome as described in Example 4C) and one of the lipid bilayer stabilizer drugs spermidine or chloroquine showed a delay in the development of this pathology. H308 monoclonal antibody was administered by intraperitoneal injection of 1 mg each week for 2 months to BALB/c female mice, and simultaneously the stabilizer drug chloroquine was administered at 2.5 mg/Kg of body weight, oral doses each 24 hs, over two months. With this treatment the development of mice pathology induced by H308 monoclonal antibody was delayed. It is possible that by modifying the doses of stabilizers drugs that are applied to mice it is possible to prevent the development of these illnesses. The chloroquine dose used was similar to the one used in humans in the treatment of rheumatoid arthritis and of systemic lupus erythematosus.

Spermidine was administered, as a chlorhydrate, in a dose of 1 mg/Kg of body weight, by intraperitoneal injection each 24 hs, over two months. Using this spermidine dose, results similar to those described with chloroquine were obtained.

According to the above-mentioned studies the therapeutically effective quantity of the lipidic bilayer stabilizer drug chloroquine is of 2.5 mg/Kg of body weight and of spermidine is of 1 mg/Kg of body weight.

In accordance with the information described in this work, one will be able to observe that antibodies obtained by using lipidic structures different from lipid bilayers can be used to determine cellular physiologic states and for the diagnosis and/or treatment of diseases designed to allow early detection of diseases associated with antiphospholipid antibodies and, as a consequence, to allow treatment to prevent, to stop and to reverse this disease. It will be evident for any expert in the matter that the modalities that here are presented are only illustrative and they are not to be interpreted as limiting the present invention, since other numerous changes in their details and particularities are possible without moving away from the scope of the invention.

Though specific embodiments of the invention have been illustrated and described, it is necessary to emphasize that are possible other numerous modifications to the invention, such as the use of different mice strains, lipids to obtain the liposomes, immunization methods and methods for obtaining hybridomas, diverse reagents for the diagnostic kit and/or diverse illnesses associated with antiphospholipid antibodies. Therefore, the present invention should not be considered as restricted except for which demands the previous technique and for the spirit of the annexed claims.

What is claimed:

1. A kit for detecting anti-lipidic particle antibodies in a sample from an individual suspected of suffering from an antiphospholipid syndrome, comprising:
    a) an indicator reagent comprising lipidic particle antigen that binds to anti-lipidic particle antibodies, wherein said lipidic particle antigen comprises a structural arrangement of lipids, and wherein said structural arrangement of lipids does not form a bilayer but is immersed in a bilayer;
    b) a buffer solution; and
    c) a detectable labeled reagent,
    wherein the presence of anti-lipidic particle antibodies indicates diagnosis of an illness associated with antiphospholipid antibodies.

2. The kit of claim 1, wherein said lipidic particle antigen comprises lipids induced to form lipidic particles with an agent selected from the group consisting of divalent cations and drugs producing lupus in humans, and wherein said lipidic particles are bound to microtiter plates with a high lipidic binding property or suspended.

3. The kit of claim 2, wherein said lipidic particle antigen comprises neoplastic cells and said lipidic particles are bound to a solid support selected from the group consisting of micro cover glasses and microtiter plates.

4. The kit of claim 1, wherein the buffer solution has a pH of 7.0 to 7.4.

5. The kit of claim 1, wherein the detectable labeled reagent comprises detectable labeled polyvalent anti-human immunoglobulin secondary antibodies.

6. The kit of claim 5, wherein the detectable labeled anti-human immunoglobulin secondary antibodies comprise at least one anti-human immunoglobulin antibody selected from the group consisting of anti-IgG, anti-IgM and anti-IgA.

7. The kit of claim 1, wherein the detectable labeled reagent comprises a component selected from the group consisting of enzymes and fluorochromes and said component is attached to an element selected from the group consisting of polyvalent anti-immunoglobulins, anti-IgG, anti-IgM and anti-IgA immunoglobulin secondary antibodies, wherein said enzyme is selected from the group consisting of alkaline phosphatase and peroxidase, and said fluorochrome is selected from the group consisting of fluorescein isothiocyanate, phycoerythrin and peridinin-chlorophyll-protein complex.

8. The kit of claim 1, further comprising a blocking solution and a sample of a reference serum from a healthy individual.

9. The kit of claim 1, further comprising an anti-lipidic particle polyclonal or monoclonal antibody.

10. The kit of claim 1, further comprising a protocol for the detection of the presence of anti-lipidic particle antibodies wherein the protocol is selected from the group consisting of liposomal-ELISA, cell-ELISA, immunofluorescence, liposomal-cytofluorometry and cell-cytofluorometry.

11. The kit of claim 2, wherein said lipidic particles are selected from the group consisting of liposomes, neoplastic cells, human erythrocytes, human leukocytes, and human platelets.

12. The kit of claim 11, wherein said lipidic particles are selected from the group consisting of erythrocytes, leukocytes, and platelets, and said lipidic particles are suspended in a buffer solution that provides conditions for the binding of anti-lipidic particle antibodies to the lipidic particles.

13. A kit for detecting anti-lipidic particle antibodies in a sample, comprising:
    a) antigen, containing stabilized lipidic particles;
    b) a buffer solution; and
    c) a detectable labeled reagent.

14. The kit of claim 13 wherein said antigen containing stabilized lipidic particles is liposomes treated with an agent selected from calcium ions, procainamide and chlorpromazine.

* * * * *